US007967861B2

(12) United States Patent
Montgomery et al.

(10) Patent No.: US 7,967,861 B2
(45) Date of Patent: Jun. 28, 2011

(54) DEVICES, SYSTEMS AND METHODS FOR MATERIAL FIXATION

(75) Inventors: Kenneth D. Montgomery, Roslyn, NY (US); Derek J. Harper, Scottsdale, AZ (US); Kevin N. Baird, Phoenix, AZ (US); Joe P. Kovalski, Ventura, CA (US); Joanne Kovalski, legal representative, Ventura, CA (US); David G. Spilka, Phoenix, AZ (US)

(73) Assignee: Cayenne Medical, Inc., Scottsdale, AZ (US)

( * ) Notice: Subject to any disclaimer, the term of this patent is extended or adjusted under 35 U.S.C. 154(b) by 1073 days.

(21) Appl. No.: 11/725,981

(22) Filed: Mar. 20, 2007

(65) Prior Publication Data
US 2008/0027430 A1 Jan. 31, 2008

Related U.S. Application Data

(60) Provisional application No. 60/784,422, filed on Mar. 20, 2006, provisional application No. 60/854,178, filed on Oct. 24, 2006, provisional application No. 60/898,946, filed on Jan. 31, 2007.

(51) Int. Cl.
*A61F 2/08* (2006.01)
(52) U.S. Cl. .................... 623/13.15; 623/13.14
(58) Field of Classification Search .......... 606/200–330; 16/221; 623/13.14, 13.15; 411/32, 33, 35, 411/37, 39, 40, 42, 44, 57.1, 60.2, 60.3, 80.2, 411/80.5, 80.6
See application file for complete search history.

(56) References Cited

U.S. PATENT DOCUMENTS

| 1,422,048 | A | * | 7/1922 | Goodridge ............ 16/221 |
| 3,708,883 | A | | 1/1973 | Flander |
| 3,832,931 | A | | 9/1974 | Talan |
| 4,311,421 | A | | 1/1982 | Okada et al. |
| 4,711,232 | A | | 12/1987 | Fischer et al. |

(Continued)

FOREIGN PATENT DOCUMENTS
CA 2235354 A1 10/1999
(Continued)

OTHER PUBLICATIONS

Written Opinion of the International Searching Authority, Feb. 20, 2008, corresponding to PCT Application No. PCT/US07/06928; International Search Report, Feb. 20, 2008, corresponding to PCT Application No. PCT/US/06928.

(Continued)

*Primary Examiner* — Eduardo C Robert
*Assistant Examiner* — Christian Sevilla
(74) *Attorney, Agent, or Firm* — Stout, Uxa, Buyan & Mullins, LLP; Donald E. Stout

(57) ABSTRACT

A material fixation system is particularly adapted to improve the tendon-to-bone fixation of hamstring autografts, as well as other soft tissue ACL reconstruction techniques. The system is easy to use, requires no additional accessories, uses only a single drill hole, and can be implanted by one person. Additionally, it replicates the native ACL by compressing the tendons against the aperture of the tibial tunnel, which leads to a shorter graft and increased graft stiffness. It is adapted to accommodate single or double tendon bundle autografts or allografts. It also provides pull out strength measured to be greater than 1000 N.

44 Claims, 19 Drawing Sheets

U.S. PATENT DOCUMENTS

| | | | |
|---|---|---|---|
| 4,716,893 A | 1/1988 | Fischer et al. |
| 4,738,255 A | 4/1988 | Goble et al. |
| 4,744,793 A | 5/1988 | Parr et al. |
| 4,772,286 A | 9/1988 | Goble et al. |
| 4,778,468 A | 10/1988 | Hunt et al. |
| 4,828,562 A | 5/1989 | Kenna |
| 4,870,957 A | 10/1989 | Goble et al. |
| 4,955,910 A | 9/1990 | Bolesky |
| 5,004,474 A | 4/1991 | Fronk et al. |
| 5,037,422 A | 8/1991 | Hayhurst et al. |
| 5,139,520 A | 8/1992 | Rosenberg |
| 5,176,709 A | 1/1993 | Branemark |
| 5,211,647 A | 5/1993 | Schmieding |
| 5,234,430 A | 8/1993 | Huebner |
| 5,236,445 A | 8/1993 | Hayhurst et al. |
| 5,258,016 A | 11/1993 | DiPoto et al. |
| 5,268,001 A | 12/1993 | Nicholson et al. |
| 5,320,626 A | 6/1994 | Schmieding |
| 5,336,240 A | 8/1994 | Metzler et al. |
| 5,350,383 A | 9/1994 | Schmieding et al. |
| 5,354,298 A | 10/1994 | Lee et al. |
| 5,356,435 A | 10/1994 | Thein |
| 5,374,269 A | 12/1994 | Rosenberg |
| 5,383,878 A | 1/1995 | Roger et al. |
| 5,411,523 A | 5/1995 | Goble |
| 5,431,651 A | 7/1995 | Goble |
| 5,456,685 A | 10/1995 | Huebner |
| 5,464,427 A | 11/1995 | Curtis et al. |
| 5,466,237 A | 11/1995 | Byrd et al. |
| 5,474,555 A | 12/1995 | Puno et al. |
| 5,480,403 A | 1/1996 | Lee et al. |
| 5,571,104 A | 11/1996 | Li |
| 5,571,184 A | 11/1996 | DeSatnick |
| 5,575,819 A | 11/1996 | Amis |
| 5,601,562 A | 2/1997 | Wolf et al. |
| 5,603,716 A | 2/1997 | Morgan et al. |
| 5,618,314 A | 4/1997 | Harwin et al. |
| 5,632,748 A | 5/1997 | Beck, Jr. et al. |
| 5,645,589 A | 7/1997 | Li |
| 5,702,215 A | 12/1997 | Li |
| 5,702,397 A | 12/1997 | Goble et al. |
| 5,707,395 A | 1/1998 | Li |
| 5,713,903 A | 2/1998 | Sander et al. |
| 5,718,706 A | 2/1998 | Roger |
| 5,725,529 A | 3/1998 | Nicholson et al. |
| 5,725,541 A | 3/1998 | Anspach, III et al. |
| 5,728,136 A | 3/1998 | Thal |
| 5,741,300 A | 4/1998 | Li |
| 5,743,912 A | 4/1998 | Lahille et al. |
| 5,769,894 A | 6/1998 | Ferragamo |
| 5,782,865 A | 7/1998 | Grotz |
| 5,814,073 A | 9/1998 | Bonutti |
| 5,845,645 A | 12/1998 | Bonutti |
| 5,871,504 A | 2/1999 | Eaton et al. |
| 5,899,938 A | 5/1999 | Sklar et al. |
| 5,902,303 A | 5/1999 | Eckhoff et al. |
| 5,911,721 A | 6/1999 | Nicholson et al. |
| RE36,289 E | 8/1999 | Le et al. |
| 5,931,869 A | 8/1999 | Boucher et al. |
| 5,935,129 A | 8/1999 | McDevitt et al. |
| 5,941,901 A | 8/1999 | Egan |
| 5,957,953 A | 9/1999 | DiPoto et al. |
| 5,961,520 A | 10/1999 | Beck, Jr. et al. |
| 5,964,764 A | 10/1999 | West, Jr. et al. |
| 5,968,078 A | 10/1999 | Grotz |
| 5,993,459 A | 11/1999 | Larsen et al. |
| 6,017,346 A | 1/2000 | Grotz |
| 6,086,608 A | 7/2000 | Ek et al. |
| 6,099,530 A | 8/2000 | Simonian et al. |
| 6,113,609 A | 9/2000 | Adams |
| 6,117,173 A | 9/2000 | Taddia et al. |
| 6,132,433 A | 10/2000 | Whelan |
| 6,146,406 A | 11/2000 | Shluzas et al. |
| 6,152,928 A | 11/2000 | Wenstrom, Jr. |
| 6,179,840 B1 | 1/2001 | Bowman |
| 6,187,008 B1 | 2/2001 | Hamman |
| 6,190,411 B1 | 2/2001 | Lo |
| 6,214,007 B1 | 4/2001 | Anderson |
| 6,221,107 B1 | 4/2001 | Steiner et al. |
| 6,325,804 B1 | 12/2001 | Wenstrom, Jr. et al. |
| 6,328,758 B1 | 12/2001 | Tornier et al. |
| 6,355,066 B1 | 3/2002 | Kim |
| 6,379,361 B1 | 4/2002 | Beck, Jr. et al. |
| 6,387,129 B2 | 5/2002 | Rieser et al. |
| 6,461,373 B2 | 10/2002 | Wyman et al. |
| 6,482,210 B1 | 11/2002 | Skiba et al. |
| 6,517,579 B1 | 2/2003 | Paulos et al. |
| 6,533,816 B2 | 3/2003 | Sklar |
| 6,554,862 B2 | 4/2003 | Hays et al. |
| 6,562,071 B2 | 5/2003 | Jarvinen |
| 6,616,694 B1 | 9/2003 | Hart |
| 6,623,524 B2 | 9/2003 | Schmieding |
| 6,632,245 B2 | 10/2003 | Kim |
| 6,648,890 B2 | 11/2003 | Culbert et al. |
| 6,656,183 B2 | 12/2003 | Colleran et al. |
| 6,716,234 B2 | 4/2004 | Grafton et al. |
| 6,736,829 B1 | 5/2004 | Li et al. |
| 6,736,847 B2 | 5/2004 | Seyr et al. |
| 6,752,831 B2 | 6/2004 | Sybert et al. |
| 6,770,073 B2 | 8/2004 | McDevitt et al. |
| 6,780,188 B2 | 8/2004 | Clark et al. |
| 6,796,977 B2 | 9/2004 | Yap et al. |
| 6,802,862 B1 | 10/2004 | Roger et al. |
| 6,833,005 B1 | 12/2004 | Mantas et al. |
| 6,887,271 B2 | 5/2005 | Justin et al. |
| 6,890,354 B2 | 5/2005 | Steiner et al. |
| 6,932,841 B2 | 8/2005 | Sklar et al. |
| 6,939,379 B2 | 9/2005 | Sklar |
| 6,942,666 B2 | 9/2005 | Overaker et al. |
| 6,942,668 B2 | 9/2005 | Padget et al. |
| 6,986,781 B2 | 1/2006 | Smith |
| 7,008,451 B2 | 3/2006 | Justin et al. |
| 7,037,324 B2 | 5/2006 | Martinek |
| 7,083,638 B2 | 8/2006 | Foerster |
| 7,201,754 B2 | 4/2007 | Stewart et al. |
| 7,309,355 B2 | 12/2007 | Donnelly et al. |
| 7,326,247 B2 | 2/2008 | Schmieding et al. |
| 7,556,629 B2 | 7/2009 | Von Hoffmann et al. |
| 7,556,640 B2 | 7/2009 | Foerster |
| 2002/0165611 A1 | 11/2002 | Enzerink et al. |
| 2003/0065391 A1 | 4/2003 | Re et al. |
| 2003/0083662 A1 | 5/2003 | Middleton |
| 2003/0109900 A1 | 6/2003 | Martinek |
| 2003/0135274 A1* | 7/2003 | Hays et al. ............ 623/13.14 |
| 2003/0199877 A1 | 10/2003 | Steiger et al. |
| 2003/0204204 A1 | 10/2003 | Bonutti |
| 2004/0024456 A1* | 2/2004 | Brown et al. ............ 623/13.15 |
| 2004/0097943 A1 | 5/2004 | Hart |
| 2004/0098052 A1 | 5/2004 | West, Jr. et al. |
| 2004/0153153 A1 | 8/2004 | Elson et al. |
| 2004/0180308 A1* | 9/2004 | Ebi et al. .................... 433/173 |
| 2004/0181240 A1* | 9/2004 | Tseng et al. ................ 606/119 |
| 2004/0199165 A1 | 10/2004 | Culbert et al. |
| 2004/0230194 A1 | 11/2004 | Urbanski et al. |
| 2004/0237361 A1 | 12/2004 | O'Connell |
| 2004/0267361 A1* | 12/2004 | Donnelly et al. .......... 623/13.14 |
| 2004/0267362 A1 | 12/2004 | Hwang et al. |
| 2005/0033289 A1 | 2/2005 | Warren et al. |
| 2005/0251260 A1* | 11/2005 | Gerber et al. ............. 623/17.13 |
| 2006/0095131 A1 | 5/2006 | Justin et al. |
| 2006/0155287 A1 | 7/2006 | Montgomery et al. |
| 2008/0119929 A1 | 5/2008 | Schmieding et al. |

FOREIGN PATENT DOCUMENTS

| | | |
|---|---|---|
| EP | 0232049 B1 | 3/1990 |
| EP | 0528573 A1 | 8/1992 |
| EP | 0688185 A1 | 2/1993 |
| EP | 1033115 A2 | 9/2000 |
| EP | 0762850 B1 | 2/2004 |
| EP | 0739185 B1 | 9/2004 |
| EP | 1011535 B1 | 12/2005 |
| FR | 2696925 A1 | 4/1994 |
| JP | 10155820 A | 6/1998 |
| WO | 8809157 | 12/1988 |
| WO | W09216167 A1 | 10/1992 |
| WO | WO9515726 A1 | 6/1995 |
| WO | WO9812991 A1 | 4/1998 |

| | | |
|---|---|---|
| WO | 9818409 | 5/1998 |
| WO | 0130253 A1 | 5/2001 |
| WO | WO02085256 A1 | 10/2002 |

OTHER PUBLICATIONS

Caborn et al., A Biomechanical Comparison of Initial Soft Tissue Tibial Fixation Devices: The Intrafix Versus a Tapered 35-mm Bioabsorbable Interference Screw, The American Journal of Sports Medicine, 2004, vol. 32, No. 4.

Charlton et al., Clinical Outcome of Anterior Cruciate Ligament Reconstruction with Quadrupled Hamstring Tendon Graft and Bioabsorbable Interference Screw Fixation, The American Journal of Sports Medicine, 2003, pp. 518-521, vol. 31, No. 4, Kerlan-Jobe Orthopaedic Clinic, Los Angeles.

Morgan et al., Anatomic Graft Fixation Using a Retrograde Biointerference Screw for Endoscopic Anterior Cruciate Ligament Reconstruction: Single-Bundle and 2-Bundle Techniques, Techniques in Orthopaedics, 2005, pp. 297-302, vol. 20, No. 3, Lippincott Williams & Wilkins, Inc., Philadelphia.

Robbe et al., Graft Fixation Alternatives in Anterior Cruciate Ligament Reconstruction, Spring 2002, pp. 21-28, vol. 15, Orthopaedic Surgery Department, University of Kentucky School of Medicine, Lexington, KY, U.S.A.

Scheffler et al., Biomechanical Comparison of Hamstring and Patellar Tendon Graft Anterior Cruciate Ligament Reconstruction Techniques: The Impact of Fixation Level and Fixation Method Under Cyclic Loading, Arthroscopy: The Journal of Arthroscopic and Related Surgery, Mar. 2002, pp. 304-315, vol. 18, No. 3, Arthroscopy Association of North America.

Simonian et al., Interference Screw Position and Hamstring Graft Location for Anterior Cruciate Ligament Reconstruction, The Journal of Arthroscopic and Related Surgery, Jul.-Aug. 1998, pp. 459-464, vol. 14, No. 5, The New York Hospital—Cornell University Medical College, New York, U.S.A.

Wolf, Eugene M., Hamstring Anterior Cruciate Ligament, Reconstruction using Femoral Cross-pin Fixation, Operative Techniques in Sports Medicine, Oct. 1999, pp. 241-222, vol. 7, No. 4, W.B. Saunders Company, San Francisco, U.S.A.

A Biomechanical Comparison of Femoral RetroScrew Placement in a Porcine Model, Arthrex Research and Development, 2007, Arthex, Inc.

Scope This Out: A Technical Pearls Newsletter for Arthroscopists, Fall 1999, vol. 1, No. 3, Arthrex, Inc, U.S.A.

Scope This Out: A Technical Pearls Newsletter for Arthroscopists, Summer 2001, vol. 3, No. 2, Arthrex, Inc, U.S.A.

Scope This Out: A Technical Pearls Newsletter for Arthroscopists, Summer 2002, vol. 4, No. 2, Arthrex, Inc, U.S.A.

Scope This Out: A Technical Pearls Newsletter for Arthroscopists, Summer 2002, vol. 5, No. 2, Arthrex, Inc, U.S.A.

* cited by examiner

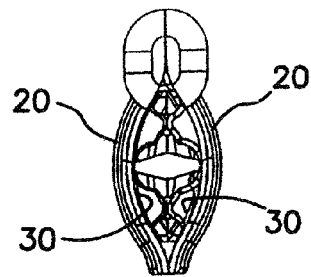
FIG. 22
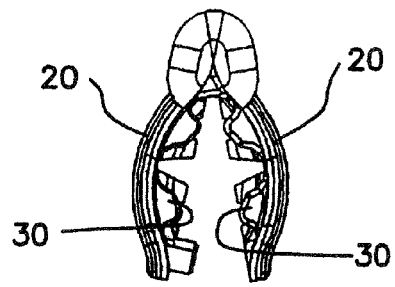
FIG. 24
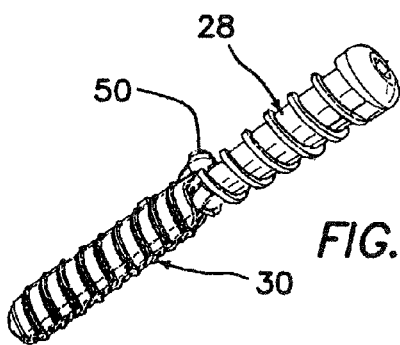
FIG. 23
FIG. 25
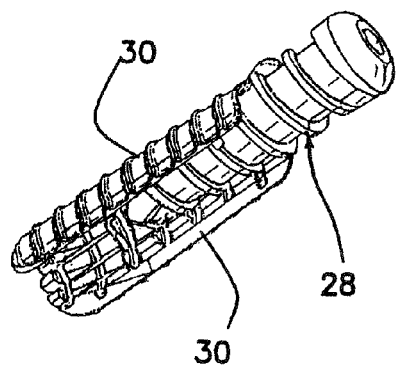
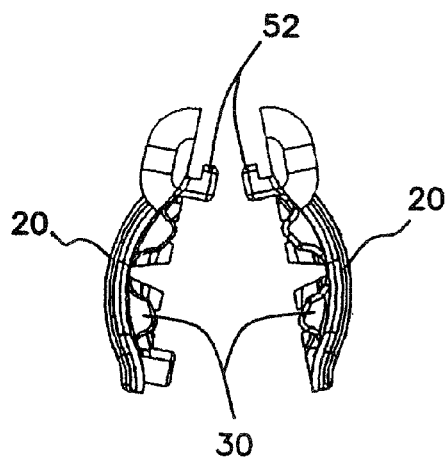
FIG. 26
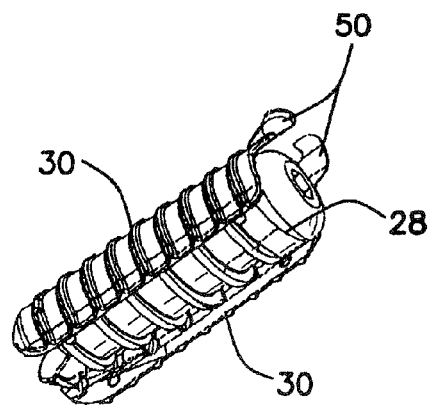
FIG. 27

| | | Pull out Forces (N) |
|---|---|---|
| Implants | Mean | 1253 |
| | Standard Deviation | 142.5 |
| | Minimum Value | 938.3 |
| | Maximum Value | 1567.9 |
| | | Pull out Forces (N) |
| RCI Screws | Mean | 532.7 |
| | Standard Deviation | 349.7 |
| | Minimum Value | 135.7 |
| | Maximum Value | 1230.9 |

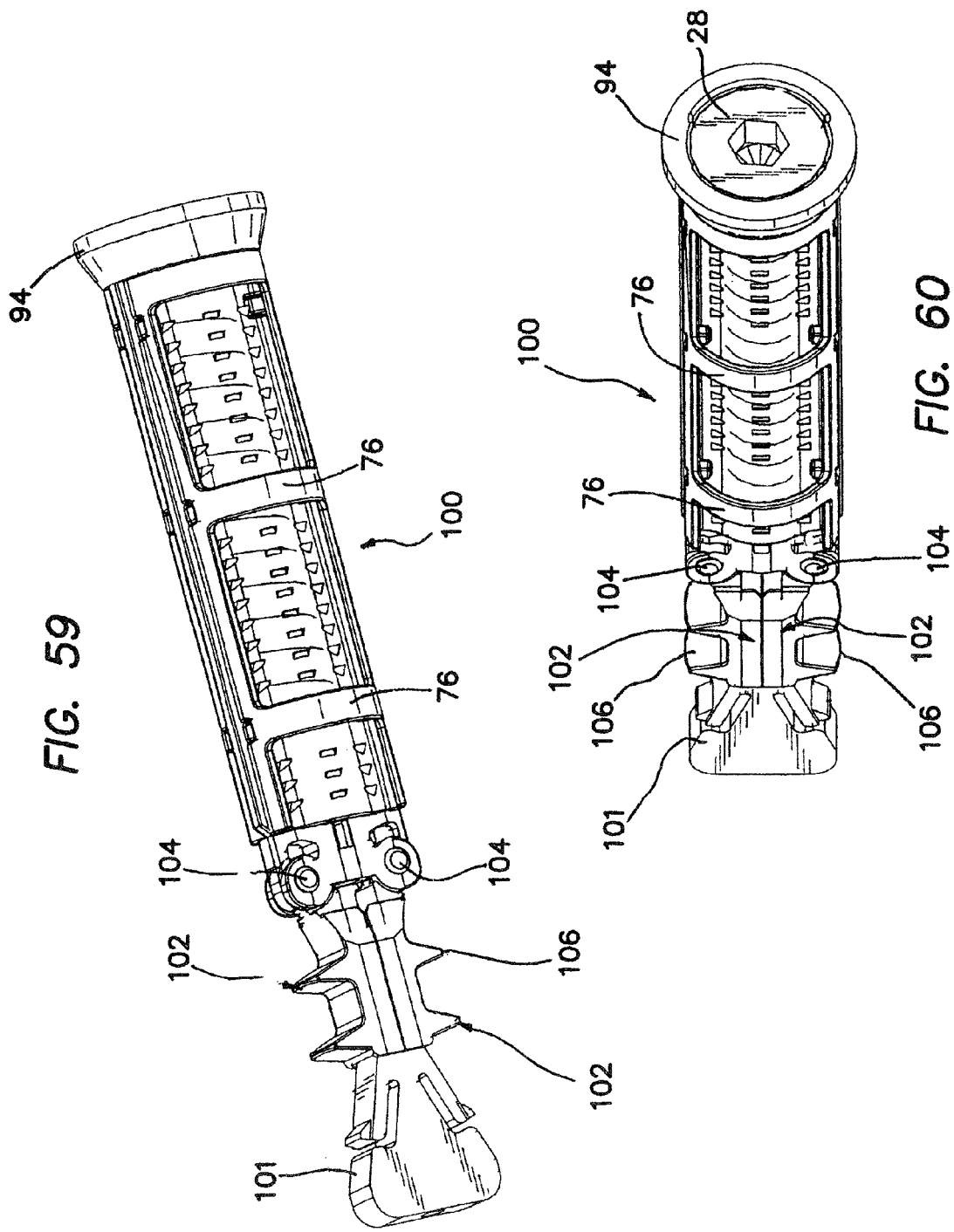

DEVICES, SYSTEMS AND METHODS FOR MATERIAL FIXATION

This application claims the benefit under 35 U.S.C. 119(e) of the filing date of Provisional U.S. Application Ser. No. 60/784,422, entitled Method and Apparatus for Attaching Soft Tissues to Bone, filed on Mar. 20, 2006, and of the filing date of Provisional U.S. Application Ser. No. 60/854,178, entitled Methods and Systems for Material Fixation, filed on Oct. 24, 2006, and of the filing date of Provisional U.S. Application Ser. No. 60/898,946, entitled Devices, Systems and Methods for Material Fixation, filed on Jan. 31, 2007. All of these prior provisional applications are expressly incorporated herein by reference.

BACKGROUND OF THE INVENTION

The present invention relates generally to devices, systems and methods for material fixation. More specifically, the present invention relates to a soft tissue or bone-to-bone fixation system that permits a practitioner to repair many soft tissue injuries, such as an Anterior Cruciate Ligament (ACL) injury.

One of the most common needs in orthopedic surgery is the fixation of tendon to bone. The fixation of diseased tendons into a modified position is called tenodesis and is commonly required in patients with injury to the long head of the biceps tendon in the shoulder. In addition, tendons which are torn from their insertion site into bone also frequently require repair. This includes distal biceps tendon tears, rotator cuff tears, and torn flexor tendons in the hand. Tendons are also frequently used in the reconstruction of unstable joints. Common examples include anterior cruciate ligament and collateral ligament reconstructions of the knee, medial and lateral elbow collateral ligament reconstructions, ankle collateral ligament reconstruction, finger and hand collateral ligament reconstructions and the like.

Traditional techniques that are used to fix tendon to bone suffer from a number of limitations as a result of the methodology used, including the use of a "keyhole" tenodesis, pull-out sutures, bone tunnels, and interference screw fixation. The "keyhole" tenodesis requires the creation of a bone tunnel in the shape of a keyhole, which allows a knotted tendon to be inserted into the upper portion, and subsequently wedged into the lower narrower portion of the tunnel where inherent traction on the tendon holds it in place. This technique is challenging as it is often difficult to sculpt the keyhole site and insert the tendon into the tunnel. In addition, if the tendon knot unravels in the postoperative period, the tendon will slide out of the keyhole, losing fixation.

Another traditional form of tendon fixation is the use of the "pull-out stitch." With this technique, sutures attached to the tendon end are passed through bone tunnels and tied over a post or button on the opposite side of the joint. This technique has lost favor in recent years due to a host of associated complications, which include wound problems, weak fixation strength, and potential injury to adjacent structures.

The most common method of fixation of tendon to bone is the use of bone tunnels with either suture fixation, or interference screw fixation. The creation of bone tunnels is relatively complicated, often requiring an extensive exposure to identify the margins of the tunnels. Drill holes placed at right angles are connected using small curettes. This tedious process is time-consuming and fraught with complications, which include poor tunnel placement and fracture of the overlying bone bridge. Graft isometry, which is easy to determine with single point fixation, is difficult to achieve because the tendon exits the bone from two points. After creation of tunnels, sutures must be passed through the tunnels to facilitate the passage of the tendon graft. Tunnels should be small enough to allow good tendon-bone contact, yet large enough to allow for graft passage without compromising the tendon. This portion of the procedure is often time-consuming and frustrating to a surgeon. Finally, the procedure can be compromised if the bone bridge above the tunnel breaks, resulting in loss of fixation. The technique restricts fixation to the strength of the sutures, and does not provide any direct tendon to bone compression.

More recent advances in the field of tendon fixation involve the use of an internally deployed toggle button, for example, the ENDOBUTTON, and the use of interference screws to provide fixation. The ENDOBUTTON allows the fixation of tendon into a bone tunnel by creating an internally deployed post against a bony wall. While this technique eliminates the need for secondary incisions to place the post, the fixation strength is limited to suture strength alone. This technique does not provide direct tendon to bone compression; as such this technique may slow healing and lead to graft tunnel widening due to the "bungee effect" and "windshield wiper effect". As a result, this technique has limited clinical applications and is used primarily for salvage when bone tunnels break or backup fixation is important.

The use of the interference screw is the most notable advance in the fixation of tendon to bone. The screw is inserted adjacent to a tendon in a bone tunnel, providing axial compression between the screw threads and the bony wall. Advantages include acceptable pull-out strength and relative ease of use. Aperture fixation, the ability to fix the tendon to bone at its entrance site, is a valuable adjunct to this technique as it minimizes graft motion and subsequent tunnel widening. Some disadvantages related to soft tissue interference screws are that they can be difficult to use, and can also cut or compromise the tendon during implantation.

The newest generation interference screw allows the ability to provide tendon to bone fixation with limited exposure. For example, the BIO-TENODESIS SCREW (Arthrex, Inc.) allows the tensioning and insertion of tendon into bone, followed by insertion of an adjacent soft tissue interference screw. While this screw system provides advantages in the insertion of tendon into bone in cases when a pull through stitch is not available, it is still limited by the potential for tendon rotation or disruption as the screw compresses the tendon. The surgical technique is also complicated, typically requiring two or more hands for insertion, making it difficult to use the system without assistance during arthroscopic or open procedures. Finally, the use of the screw requires preparation of the tendon end, which can be difficult, time consuming, and can also require conversion of an arthroscopic procedure to open.

Focusing particularly on the ACL, current ACL repairs utilizing soft tissue for the replacement graft are either difficult to perform or they result in less than favorable outcomes due to their relatively low tendon-to-bone fixation. Existing ACL reconstruction techniques that have acceptable outcomes (high tendon-to-bone fixation) involve extra operating room time and surgeon effort due to the requirement of multiple drill holes, external guides and fixtures for the drill holes, and multiple assistants. Moreover, these approaches to not closely replicate the native ACL in its anatomy or physiology.

Two important factors in replicating the native ACL are aperture compression and tendon length. Compressing the tendons at the aperture of the femoral tunnel will improve the healing process by increasing the intimate contact between the tendon and the bone. A study shows that without intimate contact between the tendon and the bone, the result is a graft having less well organized fibrous tissue and lower pull-out strength. The stiffness of the repair is also important to replicate the native ACL. Graft stiffness is decreased by the length of tendon between the fixation points.

Currently, two different sources are utilized for the tissue that replaces the injured native ACL. When the new tissue comes from the patient's own body, the new graft is referred to as an "autograft", and when cadaveric tissue is used, the new graft is referred to as an "allograft". The most common autograft ACL reconstruction performed currently is the bone-patellar-tendon-bone (BTB) graft. The BTB graft with an interference screw is used more often because it more accurately replicates the native ACL due to its aperture compression at the tibial tunnel aperture. However, BTB reconstructions result in an increased rate of anterior knee pain post-surgically for periods of up to three years after the reconstruction. Additionally, the harvest procedure for the BTB autograft is invasive and can be difficult to perform. Alternatively, the hamstring tendon autograft ACL reconstruction technique does not result in any significant post-surgical pain, and the harvest procedure is not minimally invasive. The reason that the hamstring tendon autograft procedure is not more frequently used in ACL reconstructions is that the fixation of the hamstring tendons to the femur an tibia, using prior art techniques, is not as strong as the fixation of the BTB autografts.

Many systems have addressed some of the problems associated with ACL reconstruction using hamstring tendons, but there is not any system which addresses them all. The TriTis® system available from Scandius attempts to more accurately replicate the native ACL by adding material to take up space in the tibial tunnel, resulting in more intimate contact between the tendon and the bone. However, to insert the device into the femoral tunnel, the cross sectional area must be less than the cross sectional area of the hole. There is no real compression of tendon to bone. The TriTis system also requires additional drill holes, accessories, and people to perform the procedure.

The IntraFix® system available from Mitek attempts to more accurately replicate the native ACL by using a screw to spread apart an integral four quadrant sheath. This acts to compress the four tendon strands against the bone. The system is easier to use than other alternatives, and does not need additional drill holes. However, it does require additional accessories, additional people to perform the procedure, and the four quadrant design does not accommodate certain allografts with two tendon strands, such as the tibialis.

The WasherLoc™ system, available from Arthrotek, gives increased strength, compared to other prior art systems, but does not accurately replicate the native ACL. The tendons are sized to the hole, but not compressed to the walls. There is also a greater distance between fixation points with this system, which can decrease the stiffness of the repair.

Interference screws such as the RCI™ Screw available from Smith & Nephew are easy to use and provide compression of tendon to bone at the tibial tunnel aperture. However, the pull out strength and stiffness of the repair are significantly lower than is the case for other prior art systems.

Thus, although there are many conventional techniques used for the fixation of tendon to bone, each having some advantages, the disadvantages of each such technique presents a need in the art for a simple and universal technique to fixate tendon to bone such that the device is easy to use, the process is simple to follow, and the result is a firm and secure tendon to bone fixation with minimal negative effect on the tendon. Further, such device should be easy to manufacture, universally applied to different tendon to bone sites, and require minimal effort to understand and use in practice.

SUMMARY OF THE INVENTION

The present invention is a system which is particularly adapted to improve the tendon-to-bone fixation of hamstring autografts, as well as other soft tissue ACL reconstruction techniques. The system is easy to use, requires no additional accessories, uses only a single drill hole, and can be implanted by one person. Additionally, it replicates the native ACL by compressing the tendons against the aperture of the tibial tunnel, which leads to a shorter graft and increased graft stiffness. It is adapted to accommodate single or double tendon bundle autografts or allografts. It also provides pull out strength measured to be greater than 1000 N, which is equivalent to or substantially higher than any of the high strength implants currently available on the market.

More particularly, a material fixation system is provided, which comprises two sheath portions defining a space therebetween, and a hinge for attaching the sheath portions together along one side thereof. An insertion member, preferably a tapered screw, is insertable into the space for expanding the sheath portions laterally outwardly in order to urge a soft tissue graft against an adjacent bone surface. In a preferred embodiment, the hinge comprises a hinge protrusion disposed on a first of the sheath portions and a hinge slot disposed on a second of the sheath portions, wherein the hinge protrusion and the hinge slot engage one another. A second hinge protrusion is disposed on the second sheath portion and a second hinge slot is disposed on the first sheath portion, wherein the second hinge protrusion and the second hinge slot also engage one another.

A driver is utilized for engaging and moving the insertion member. A hex opening is provided in the proximal end of the insertion member for engaging a distal end of the driver.

Preferably, the screw has a bullnose screw head, and the two sheath portions are mirror images of one another.

The invention is particularly advantageous, in that the system is adapted for use whether the soft tissue graft comprises an autograft, or an allograft. A distal end of the screw comprises a cut-out portion which permits the distal end of the screw to easily fit between the two sheath portions, thus permitting an operator to easily start rotation of the screw. The screw comprises external threads and the sheath portions comprise complementary internal threads. The screw further comprises a thread start to enable easier engagement of the screw threads and the sheath threads.

At least one retaining rib is preferably disposed on at least one of the sheath portions. The rib protrudes outwardly to provide a small area of higher force between the sheath portion and the soft tissue graft. The sheath portions and the insertion member are preferably adapted for insertion into a bone tunnel in a patient's tibia, and the soft tissue graft comprises a tendon graft for making an ACL repair. A cortical hook is preferably disposed on one of the sheath portions for engaging hard cortical bone at the procedural site.

One of the sheath halves preferably comprises a snap post and the other one of the sheath halves preferably comprises a complementary snap hole, wherein the snap post and the snap hole are engageable with one another to keep the two sheath halves from opening prematurely. In the preferred embodiment, a ramp is formed on one of the sheath portions for allowing a tip of the sheath portion to provide compression between the soft tissue graft and the bone at the aperture of bone tunnel in which the system is disposed. Flex grooves are disposed on one of the sheath portions, for permitting the sheath portion to flex and form around a tip of the insertion member. A bullnose sheath tip is provided on one of the sheath portions.

In some embodiments, it is advantageous for the sheath portions to further comprise a loop for retaining a soft tissue graft along a laterally outer surface of the sheath portion.

In another aspect of the invention, there is provided an implant system for promoting soft tissue to bone contact in order to promote good fixation of soft tissue to bone when making an orthopedic repair of a joint, wherein the implant system comprises a first implant adapted for receiving a tissue graft thereon and then being disposed in a first bone tunnel location, wherein ends of the tissue graft extend through a bone tunnel and out of a proximal end of the tunnel. A second implant is adapted for disposition in a second bone tunnel location, proximal to the first bone tunnel location, wherein the second implant comprises a plurality of sheaths having laterally outer surfaces and being adapted for advancing to the first bone tunnel location by sliding over the ends of the tissue graft, so that when the second implant is in the second bone tunnel location, the tissue grafts are disposed between the laterally outer surfaces of the plurality of sheaths and the bone defining the bone tunnel. An insertion member is insertable between the plurality of sheath members to laterally expand the sheath members toward the soft tissue grafts, thereby urging the soft tissue grafts into contact with the bone defining the bone tunnel.

In still another aspect of the invention, there is provided a material fixation system, which comprises a plurality of sheath portions defining a space therebetween, wherein the sheath portions are initially engaged with one another in an undeployed orientation. An insertion member is insertable into the space for expanding the sheath portions laterally outwardly to a fully deployed orientation in order to urge a soft tissue graft against an adjacent bone surface. As the sheath portions expand outwardly to the aforementioned fully deployed orientation, they become detached from one another.

In yet another aspect of the invention, there is disclosed a method of making an orthopedic repair by fixing a soft tissue graft to bone. The disclosed method comprises a step of creating a tunnel within a desired bone site, wherein the tunnel extends through a first bone member and comprises a blind hole in a second bone member. A soft tissue graft is placed on an implant. The implant is secured within the blind hole, such that a plurality of ends of the soft tissue graft extend from the implant and substantially entirely through the tunnel in the first bone member. A second implant is then slid along the soft tissue graft ends into the tunnel in the first bone member, to a predetermined location. The second implant is then expanded outwardly to compress the soft tissue graft ends against the bony wall of the bone tunnel.

The invention, together with additional features and advantages thereof, may best be understood by reference to the following description taken in conjunction with the accompanying illustrative drawing.

BRIEF DESCRIPTION OF THE DRAWINGS

FIG. 22 shows the undeployed tibial implant;
FIG. 23 shows the undeployed screw and sheath combination;
FIG. 24 shows the tibial implant as it is in the process of being deployed;
FIG. 25 shows the screw rotated to cause the sheaths to start to deploy and rotate on their hinges as shown in FIG. 24;
FIG. 26 shows the fully deployed tibial implant;
FIG. 27 shows the fully inserted screw, with the sheaths separated and fully deployed, as shown in FIG. 26.

FIG. 59 is another view of the embodiment of FIG. 58; and

FIG. 60 is still another view of the embodiment of FIGS. 58-59.

DESCRIPTION OF THE PREFERRED EMBODIMENT

Figure 1:
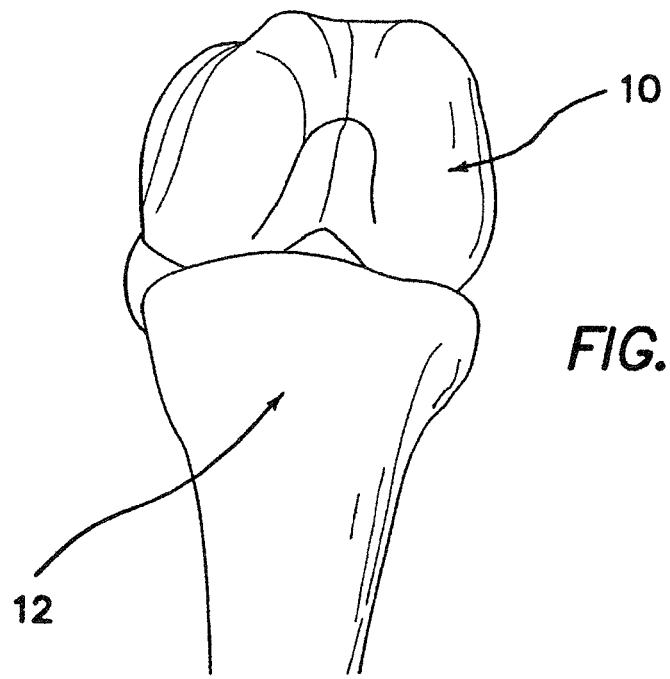
FIG. 1 is a view of the femur and tibia of a patient's leg.
Figure 2:
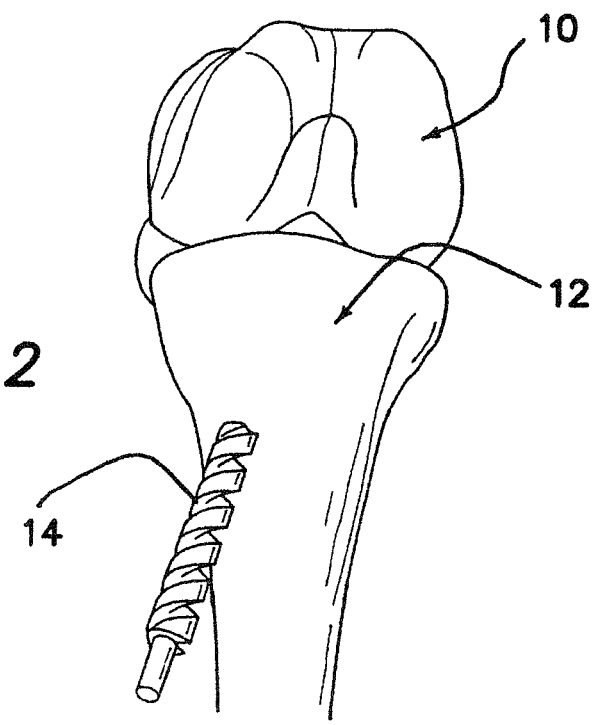
FIG. 2 is a view similar to FIG. 1, showing the use of a drill bit to make an access tunnel in the femur; and a corresponding blind hole in the tibia.
Figure 3:
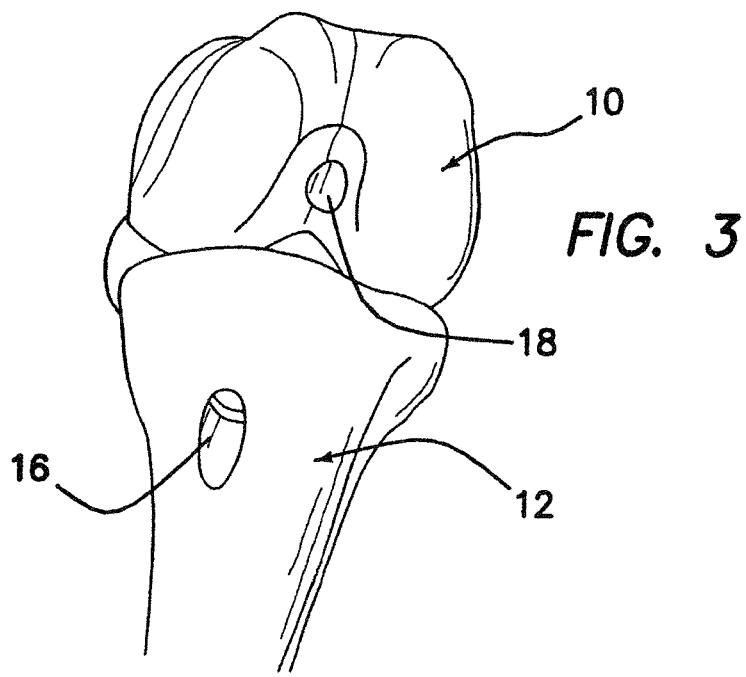
FIG. 3 is a view similar to FIGS. 1 and 2 showing the femur and tibia after the drilling step has been completed.

Referring now more particularly to the drawings, procedures and anchoring devices for repairing a patient's knee, by securing a graft of soft tissue therein, connected between the patient's femur and tibia, are illustrated. There is shown in FIG. 1 a view of a femur 10 and a tibia 12 of a patient's knee. FIG. 2 illustrates the same knee structure, wherein a drill bit 14 is utilized to drill a tunnel in the tibia 12, and a blind hole corresponding to the tunnel in the femur 10. The tibial tunnel 16 and femur blind hole 18 are shown in FIG. 3.

Figure 5:
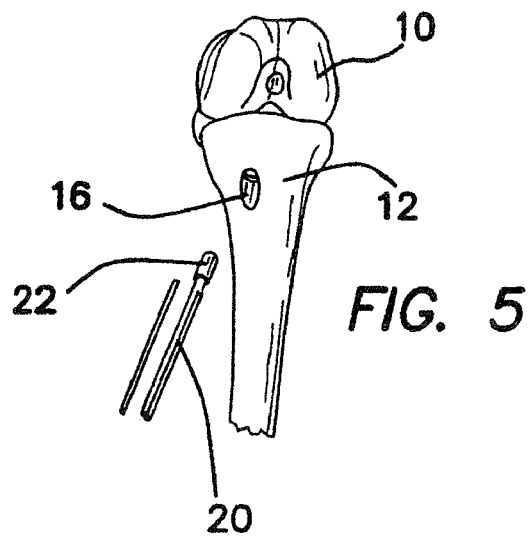
FIG. 5 is a view showing a soft tissue graft pre-loaded onto a femoral implant for use in a graft procedure performed in accordance with the principles of the present invention.

As shown in FIG. 5, a tendon bundle 20 is pre-loaded onto a femoral implant 22. In a preferred embodiment, the tendon bundle 20 is comprised of a soft tissue graft comprising a portion of a hamstring (such as pre-harvested semitendinosus and gracilis grafts), but any soft tissue may be used. Details of a presently preferred femoral implant are disclosed in co-pending provisional patent application Ser. No. 60/854,178, which has already been expressly incorporated herein by reference. However, the invention may be utilized with any suitable femoral implant.

Figure 6:
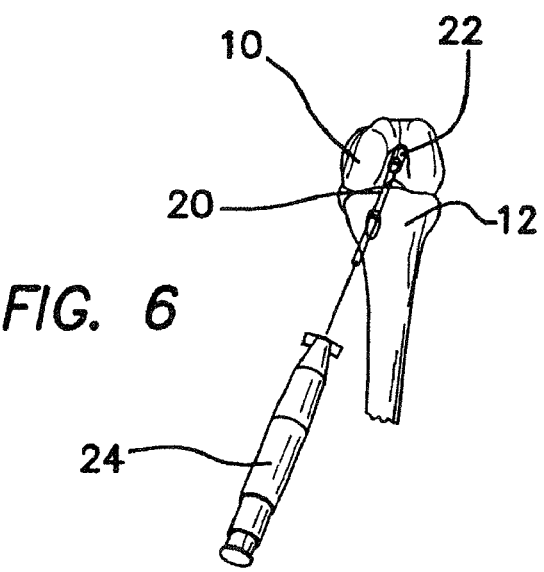
FIG. 6 is a view showing the femoral implant being inserted into the femoral socket and deployed.
Figure 7:
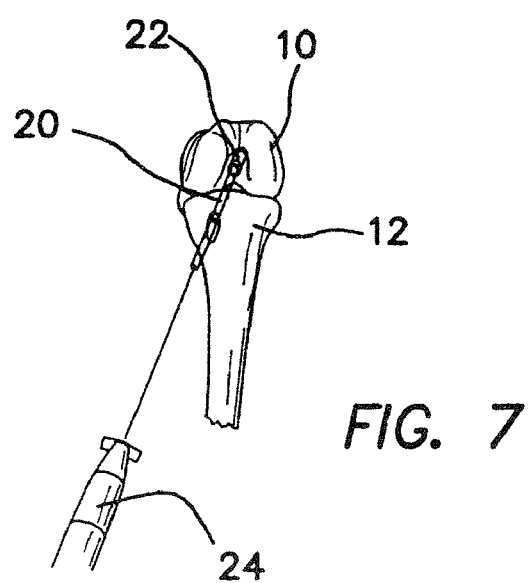
FIG. 7 is a view showing the femoral implant inserted being disengaged from the deployed femoral implant.

In FIG. 6, a femoral implant inserter 24 is utilized to insert the femoral implant into the femoral socket, wherein it is deployed. Following this, as shown in FIG. 7, the femoral implant inserter 24 is disengaged from the deployed implant 22, and withdrawn.

Figure 4:
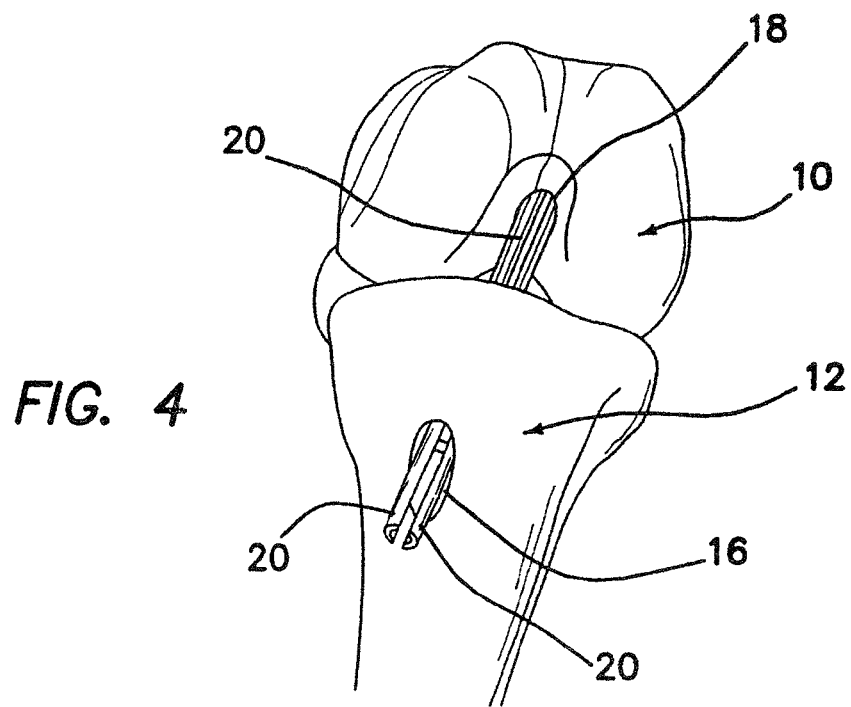
FIG. 4 is a view similar to FIGS. 1-3, after a femoral anchor has been installed into the femur access hole, illustrating graft tendon bundles extend from the femoral anchor through the tibia access tunnel.

In FIG. 4, the femoral anchor (not shown) has already been inserted into the femur blind hole 18 for securing the tendon bundle 20 therein, as shown. As is illustrated, the tendon bundles 20 extend from the femoral anchor in the femur hole 18 down through the tibial tunnel 16.

Figure 8:
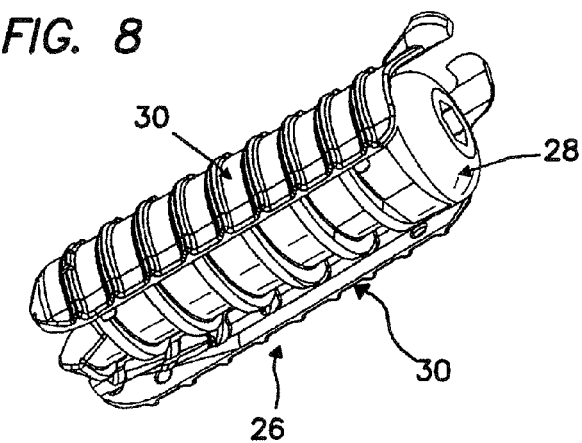
FIG. 8 is an isometric view of an embodiment of a tibial implant constructed in accordance with the principles of the present invention.

Referring now to FIGS. 8-10 and 12-18, there is shown a first, and presently preferred, embodiment of a tibial implant 26 constructed in accordance with the principles of the present invention. As shown in FIG. 8, the implant 26 comprises a tapered screw 28 and two sheath portions, or halves 30. The two sheath halves 30 are preferably mirror images of one another.

Figure 9:
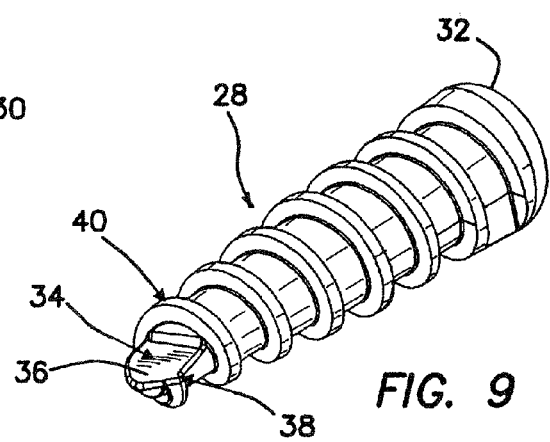
FIG. 9 is a perspective view of a screw portion of the tibial implant of FIG. 8.
Figure 10:
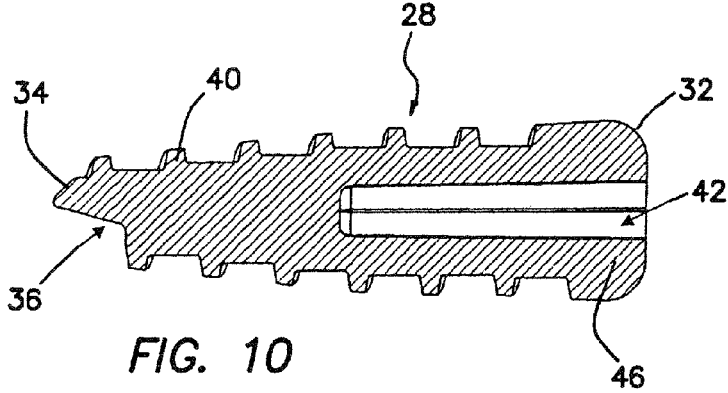
FIG. 10 is a cross-sectional view of the screw portion of FIG. 9.
Figure 11:
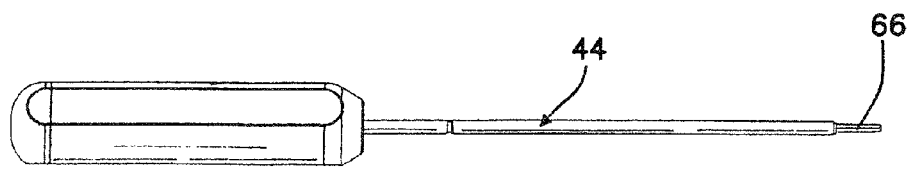
FIG. 11 is a driver used to deploy the tibial implant of the present invention.
Figure 12:
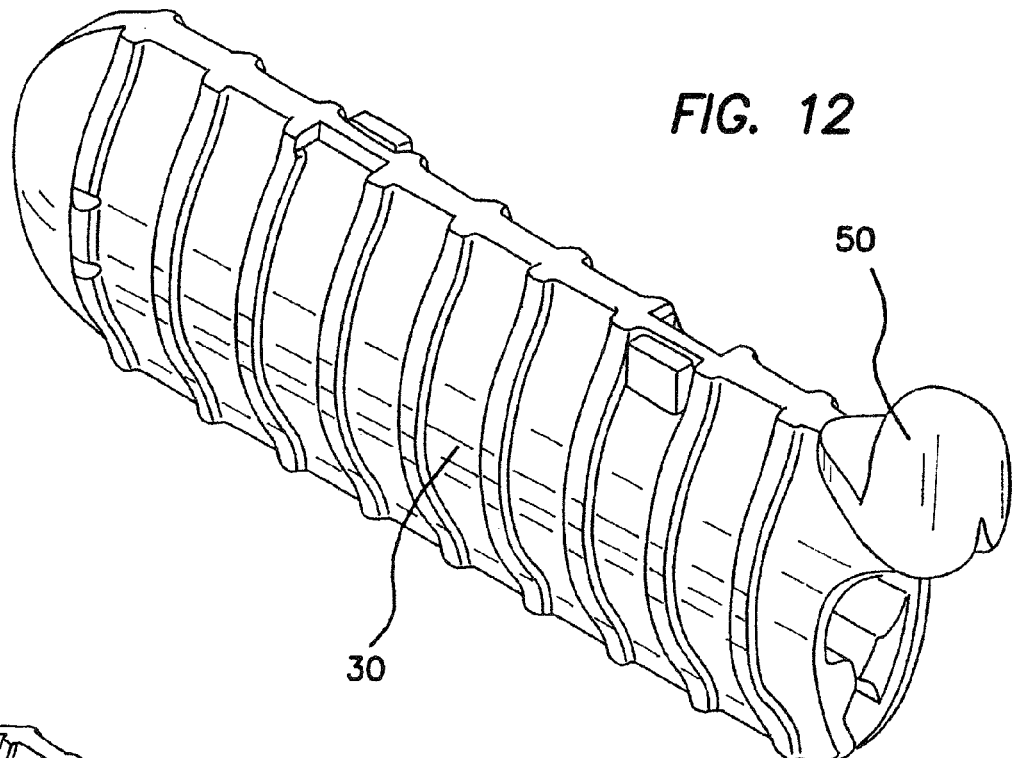
FIG. 12 is a perspective view of an assembled tibial implant according to the present invention.
Figure 13:
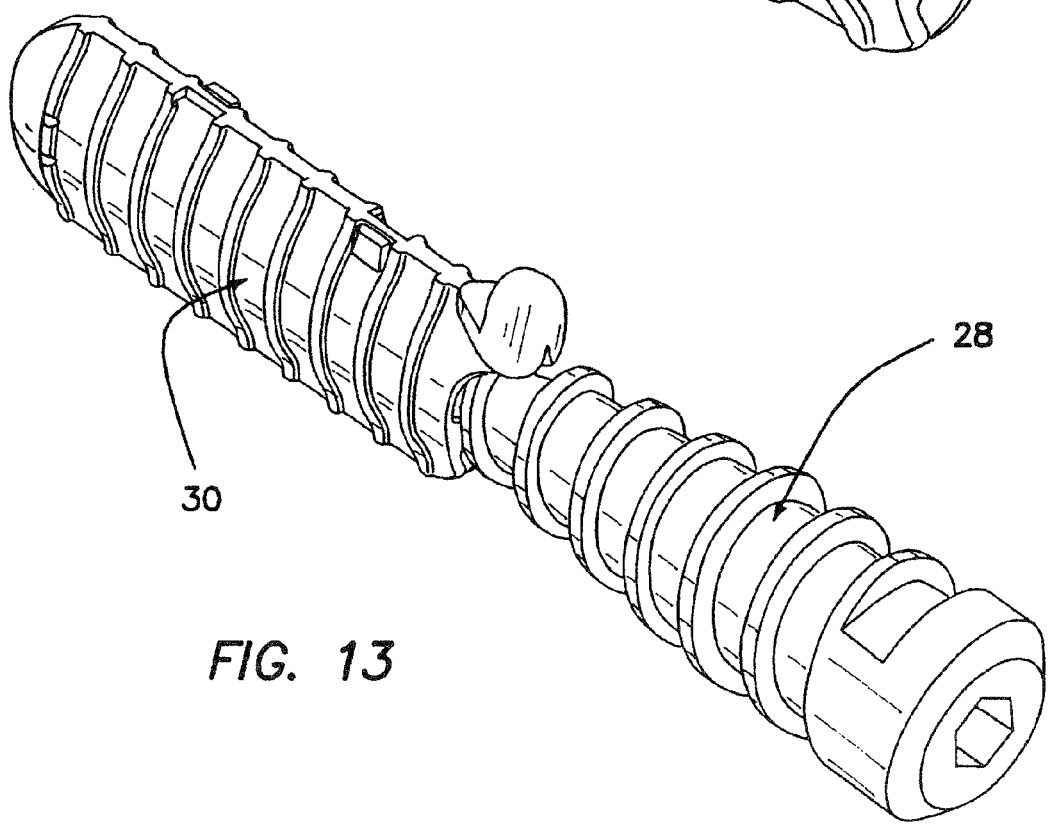
FIG. 13 is a perspective view of a disassembled tibial implant according to the present invention.
Figure 14:
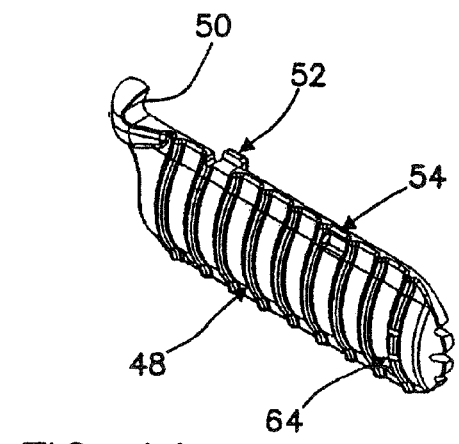
FIG. 14 is a perspective view of an exterior surface of one tibial sheath which forms a part of the tibial implant of the present invention.
Figure 15:
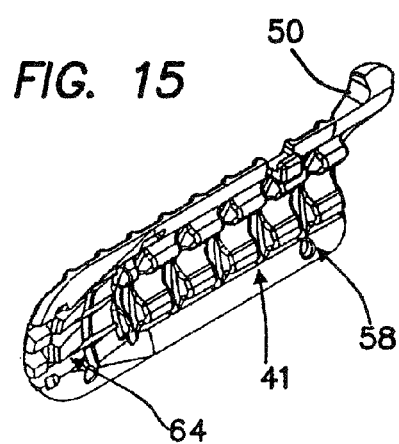
FIG. 15 is a perspective view of an interior surface of the sheath of FIG. 14.
Figure 16:
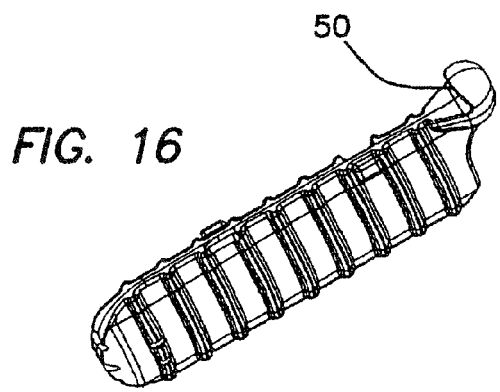
FIG. 16 is a perspective view of an assembled tibial sheath according to the present invention, shown from a first side thereof.
Figure 17:
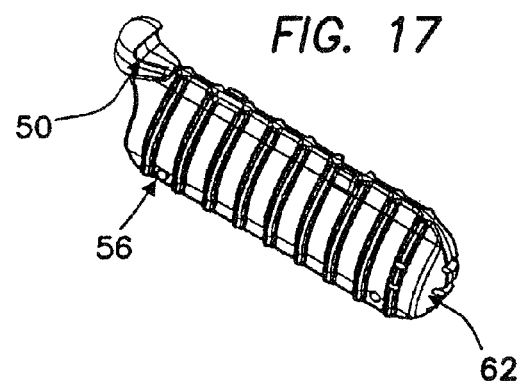
FIG. 17 is a perspective view of the sheath of FIG. 16 shown from a second side thereof.
Figure 18:
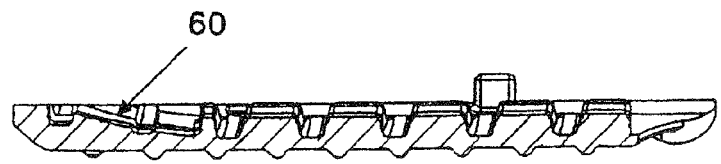
FIG. 18 is a top view of the sheath of the present invention.
Figure 19:
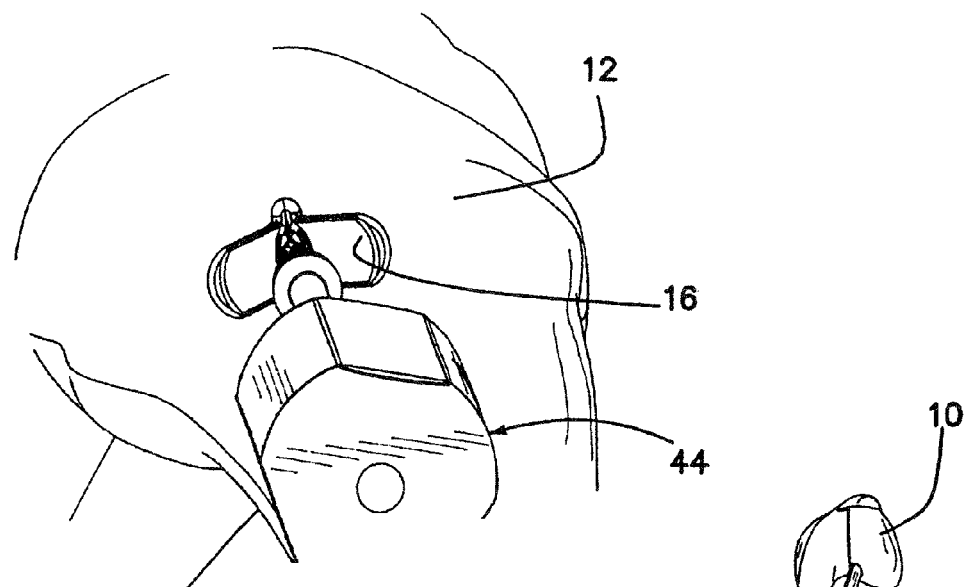
FIGS. 19-21 show the undeployed tibial implant in the tibia.
Figure 21:
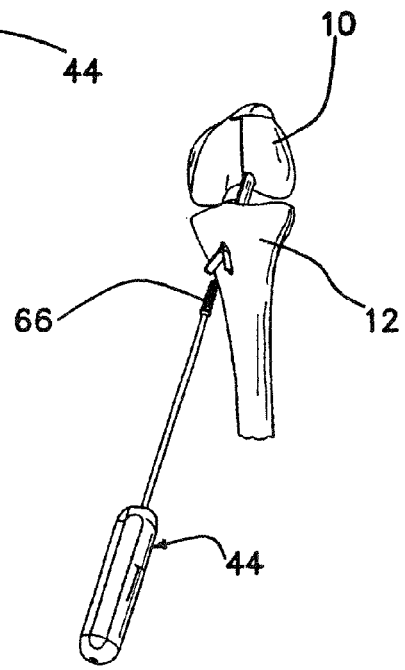
Figure 20:
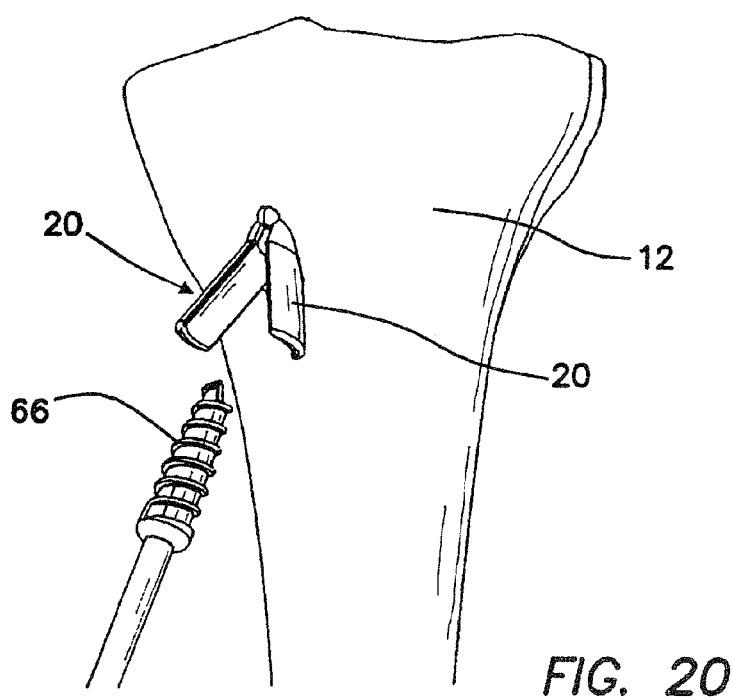

The tapered screw 28, shown particularly in FIGS. 9 and 10, has several key features. The tapered design, tapering from a relative wide proximal end 32 to a relatively narrow distal end 34, distributes the pressure between the tendon and the sheath halves 30 throughout the length of the screw 28, increasing the pull out force of the system. The screw has an easy start feature 36, which comprises a cut-out that allows the tip of the screw to fit between the sheath halves 30. With the tip between the sheaths, a thread start 38 (FIG. 10) easily engages thread 40 on the screw with an internal thread 41 of the sheath (FIG. 15) as the screw is rotated clockwise. This minimizes the force required to start the screw by reducing the distance the sheath halves 30 must be spread apart in order to start the screw. This feature also prevents the user from needing to dilate the hole between the tendon bundles. A tapered hex 42 (FIG. 10) engages with a driver 44 (FIG. 11) in order to transmit the torque required in order to deploy the screw. A bullnose screw head 46 at the proximal end 32 of the screw 28 leaves a smooth completed repair.

The sheath halves 30 have many key features as well. It is first noted that having two sheath halves 30 allows for the use of either a double or a single tendon bundle loop 20. There is no need to separate four separate ends of a double tendon bundle loop into four separate quadrants. With a double bundle loop, the implant has two free ends on either side of the sheath assembly. With a single bundle loop, one free end is in place on either side of the sheath assembly. The internal thread 41 (FIG. 15) on each sheath half 30 prevents the screw from backing out of the sheath assembly during and after deployment. The interlocking threads 40, 41 between the screw and the sheaths allow the screw to be pulled between the sheath halves 30, thus providing easier deployment. Retaining ribs 48 provide small areas of higher force between the implant and the tendon, thereby increasing the pull out force of the system.

A cortical hook 50 functions to grab the hard cortical bone of the tibia, which assists in keeping the implant in place during loading and also increases the pull out force of the system. Each sheath half 30 comprises a hinge 52 and a hinge slot 54. The hinge 52 on one sheath half 30 is placed in the hinge slot 54 of the opposing sheath half 30. This feature permits the sheath to consistently open up in one direction, as shown in FIGS. 22, 24, and 26, thus providing a repeatable deployment mode. One sheath half 30 has two snap posts 56, and the opposing sheath half 30 has a snap hole 58. These features keep the sheath halves 30 from opening prematurely. A screw ramp 60 (FIG. 18) allows for the tip of the sheath to provide compression between the tendon and the bone at the aperture of the tibial tunnel. A bullnose sheath tip 62 provides for a smooth transition between the implant system and the exit of the tibial tunnel. This reduces any stress concentrations that could sever the tendon bundle 20.

Another feature that reduces stress concentrations at the tip of the sheath halves 30 are flex grooves 64. These grooves 64 allow the sheath halves 30 to flex and form around the tip of the screw 28.

Now with reference to FIGS. 19-28, the deployment of the implant 26 will be described. The sheath halves 30 of the tibial implant 26 are disposed between the tendon bundles 20 in the tibial tunnel 16, which extend proximally through the tibial tunnel 16 from the femoral implant. The sheath halves 30 are advanced distally through the tunnel 16 until the cortical hook 50 is flush with the cortical surface of the tibia. The hook is aligned to the top of the tibial tunnel. The graft is then tensioned by pulling the tendons 20 taut, using manual traction, tensioning pulleys, or other suitable means. Again, it is noted that the primary objective with respect to the tibial anchoring solution is to ensure that good aperture fixation is achieved, and to ensure that cancellous bone fixation is not entirely relied upon. Some type of cortical fixation or backup is required to ensure a good and permanent result.

The screw 28 is then placed on a distal end 66 of the hex driver 44 until it is fully seated. Next, the screw 28 is placed with the flat of the easy start feature 36 parallel with the midplane of the sheath halves 30. With a force applied in a direction axial to the tibial tunnel, the screw is pushed distally between the sheaths. The implant 26, in its undeployed state, is shown in FIGS. 22 and 23.

While the axial force is being applied, and the easy start feature 36 is placed between the sheaths, the screw is rotated in a clockwise direction. This further separates the sheath halves 30 and presses the tendons 20 to the wall of the tibial tunnel 16. The hinges 52, 54 along the same edge as the cortical hook are used to encourage the sheath halves to open in one direction, as shown in FIGS. 24 and 25. The screw 28 is rotated until it is fully seated when the bullnose screw head 46 is flush with the cortical surface of the tibia.

FIGS. 26 and 27 show the screw in a fully inserted state, with the sheath halves 30 separated and fully deployed. In this state, the sheath halves 30 push the tendons 20 outwardly, into contact with the tibial tunnel walls. The fully deployed implant in the tibia is shown in FIG. 28.

Figures 28, 29:
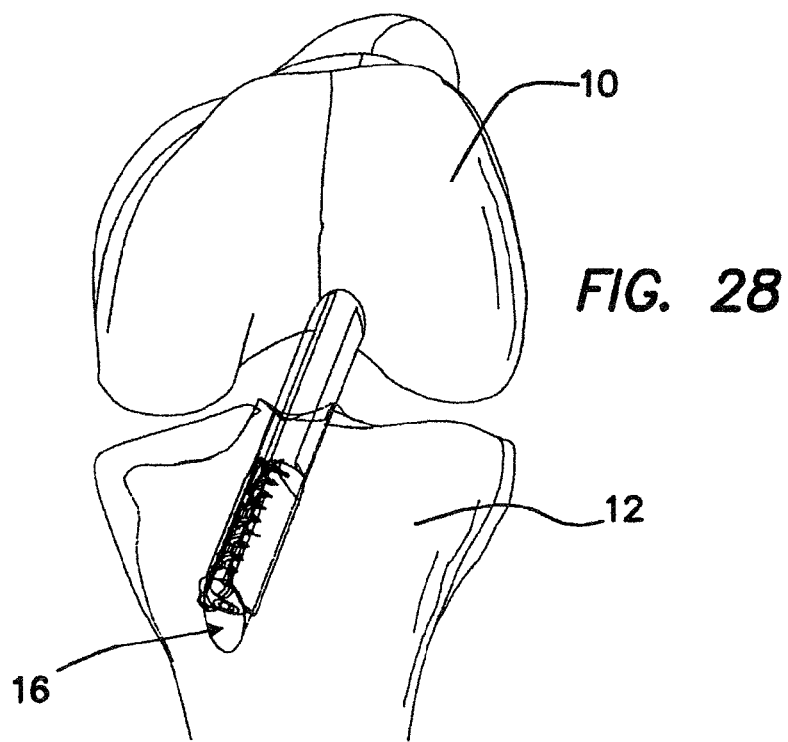
FIG. 28 is a view showing the fully deployed implant in the tibia.
FIG. 29 is a table showing measured pull out forces for an implant of the present invention, compared with the much lower pull out forces measured in a state of the art prior art tibial implant.

As shown in FIG. 29, verification testing of the embodiment shown in FIG. 28 was completed by the inventors, relative to a prior art device which is presently considered to be state of the art. As can be seen from the table, the pull out forces for the inventive implant were significantly higher than those for the prior art device. The average pull out force for the inventive device for bovine bone was 1165.2 N, as opposed to 532.7 N for the prior art device.

Figure 30:
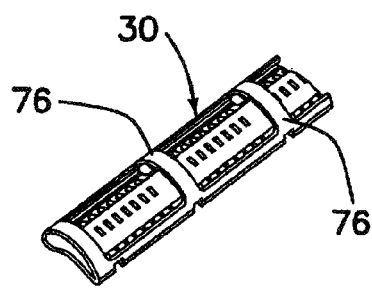
FIG. 30 is a perspective view showing a modified embodiment of a sheath which forms a part of a tibial anchor device constructed in accordance with another embodiment of the present invention.
Figure 31:
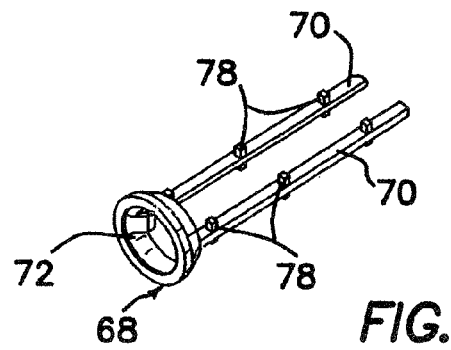
FIG. 31 is a perspective view of an anchor portion of the tibial anchor device of FIG. 30.
Figure 32:
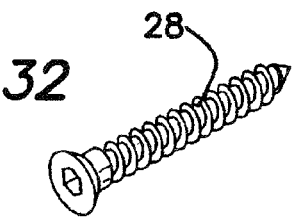
FIG. 32 is a perspective view of a screw of the tibial anchor device of FIGS. 30 and 31.
Figure 33:
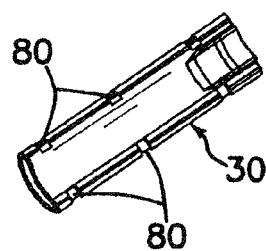
FIG. 33 is a perspective view of the opposing side of the sheath shown in FIG. 30.
Figure 34:
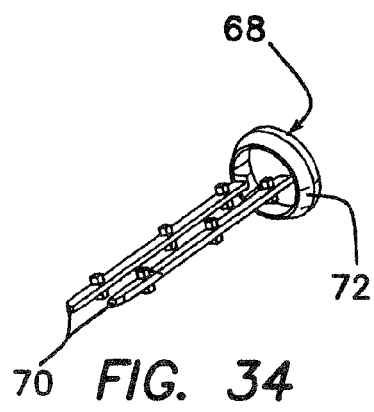
FIG. 34 is a perspective view of an opposing side of the anchor portion of FIG. 31.

Now with reference to FIGS. 30-34, various components of another embodiment of a tibial sheath anchor are illustrated. In FIGS. 30 and 33, there is shown a sheath half 30 from two opposing sides thereof. An anchor 68 is shown in FIGS. 31 and 34, and comprises a pair of legs 70 and a disk 72. A screw 28 is provided for actuating the anchor from an undeployed to a deployed configuration for securing the anchor and associated tendon bundle in place with respect to adjacent bone.

Figure 35:
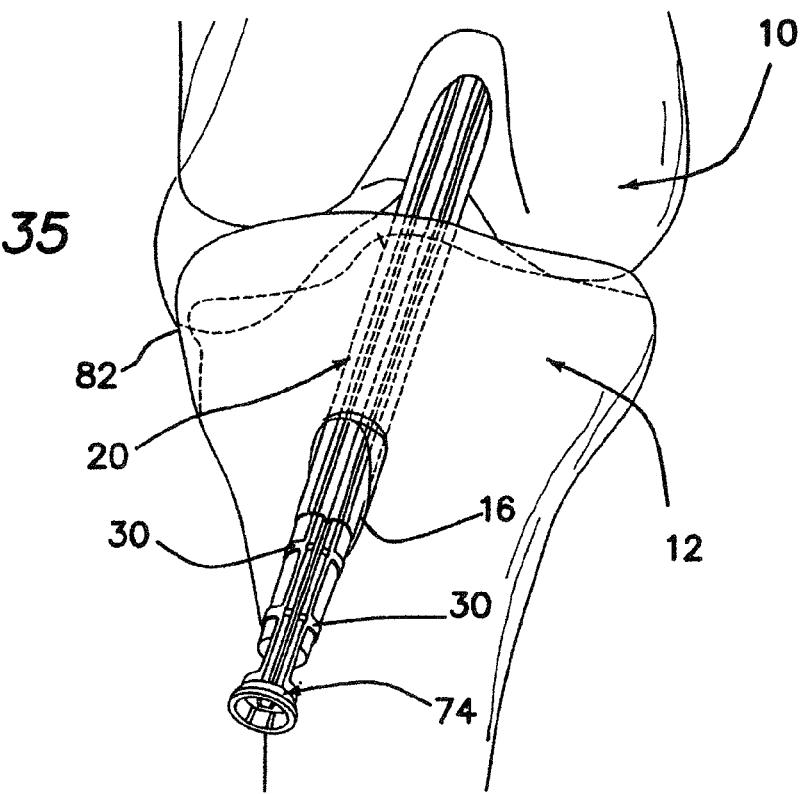
FIG. 35 is view similar to FIGS. 1-4, with portions of the bone removed in order to show the tibial anchor device of FIGS. 30-34, wherein the tendon bundles have been pulled through the sheaths of the anchor device.

Referring now to FIG. 35, the patient's femur 10 and tibia 12 are shown wherein a sheath anchor 74 is assembled and disposed for insertion into the tibial tunnel 16. In accordance with the inventive procedure, the tendon bundles 20 are pulled through the sheath halves 30, as shown, with portions of each sheath half serving to retain the tendon bundles in place adjacent to the and along the sheaths. In particular, in the illustrated embodiment, tendon loops 76 on each sheath half 30 are formed so that the tendon bundles slide lengthwise along the sheath half 30 beneath the loops 76 so that the loops perform a retention function. The anchor 74 and its legs 70 are placed between the sheath halves 30 so that square tabs 78 on the anchor legs 70 (FIG. 31) are aligned with receptacle notches 36 on the rear of the sheath half 30 (FIG. 33). The screw taper on the rear of the sheath half 30 is oriented toward the joint 82, between the femur and the tibia.

Figure 36:
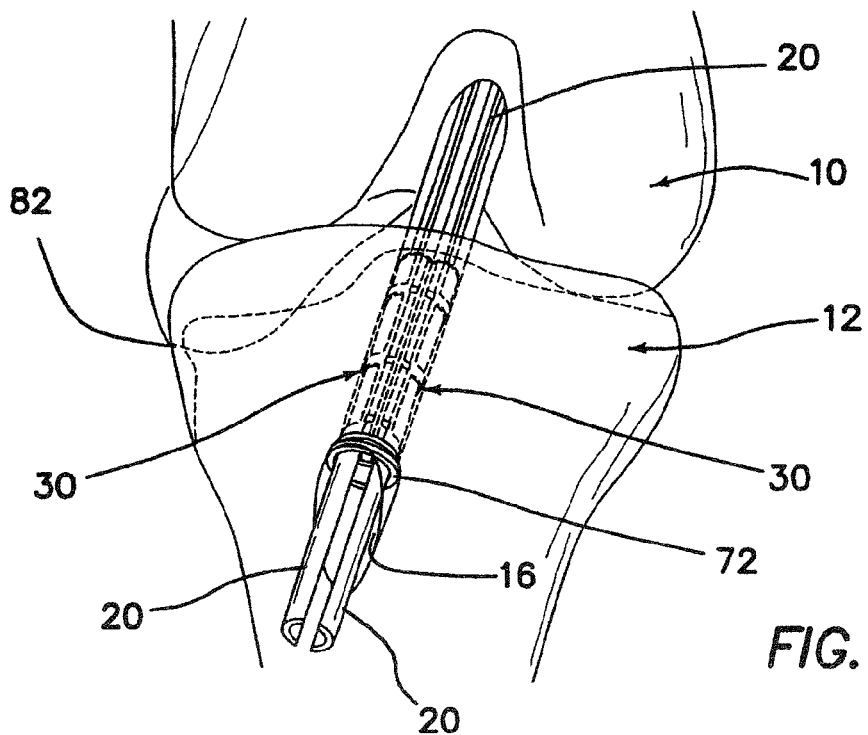
FIG. 36 is a view similar to FIG. 35 wherein the sheaths and anchor have been slid up along the tendons into the hole until the anchor bottoms out against an angular surface within the hole.
Figure 37:
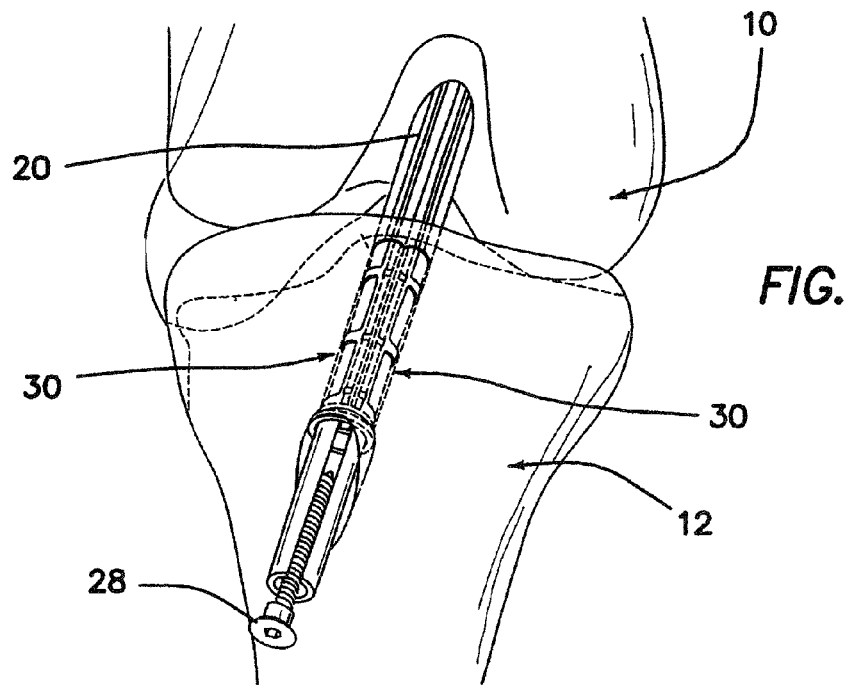
FIG. 37 is a view similar to FIG. 36, wherein tension has been applied to the tendons and the screw of FIG. 32 has been inserted into the anchor.
Figure 38:
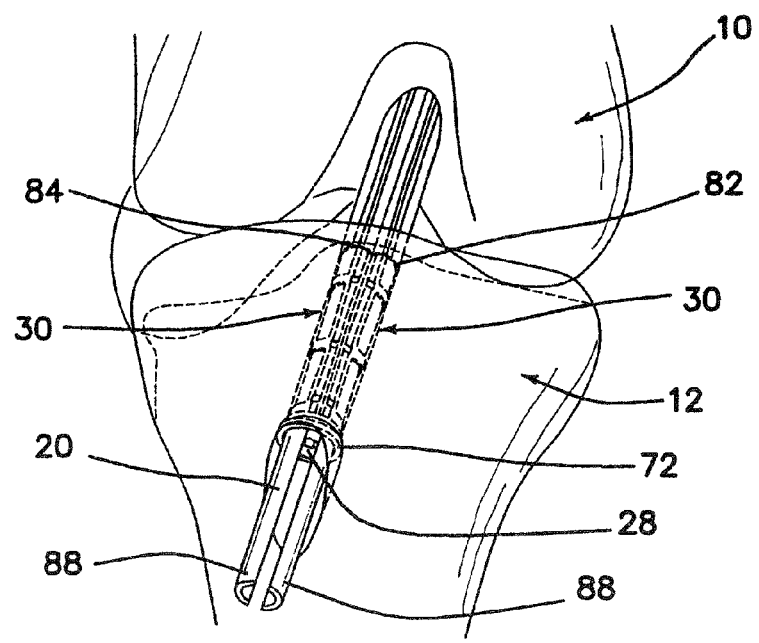
FIG. 38 is a view similar to FIG. 37, wherein the screw has been tightened until it bottoms out against the anchor.

In FIG. 36, the sheath halves 30 and anchor 68 have been slid up along the tendon bundles 20 until the anchor bottoms out against an angular surface in the hole 16. Then, as shown in FIG. 37, tension is applied to the tendon bundles 20, and the screw 28 is inserted and tightened within the anchor body, using a suitable tool, such as a hex driver. As shown in FIG. 38, the screw 28 should be tightened until it bottoms out against the anchor 68, approximately flush with or slightly recessed relative to the entrance to the tibial tunnel 16. This is important in order to ensure that there are no protrusions from the tunnels 16 which could cause discomfort to the patient or possible later complications and wear. An important advantage of the present invention is that the distal end 84 of the sheath anchor 30, as shown, for example, in FIG. 38, is disposed, once the anchor is fully inserted and deployed, so that it is in close proximity to the distal end (aperture) 86 (FIG. 49) of the tibial tunnel 16, at the joint 82. This provides excellent aperture fixation for the tendon bundles 20, in order to minimize wear on the tendon bundles over time due to the "windshield wiper" or "bungee" effects noted above in the Background of the Invention portion of the specification.

Deployment of the anchor 68 occurs when the screw 28 is inserted into the anchor body. This insertion action causes the anchor legs 70 to splay laterally outwardly, thus forcing the sheath halves 30 and tendon bundles 20 against the bony wall forming the tibial tunnel 16. As a result of this action, the tendon bundles 20 are clamped against the tibial bone 12 by the sheath halves 30.

Figure 39:
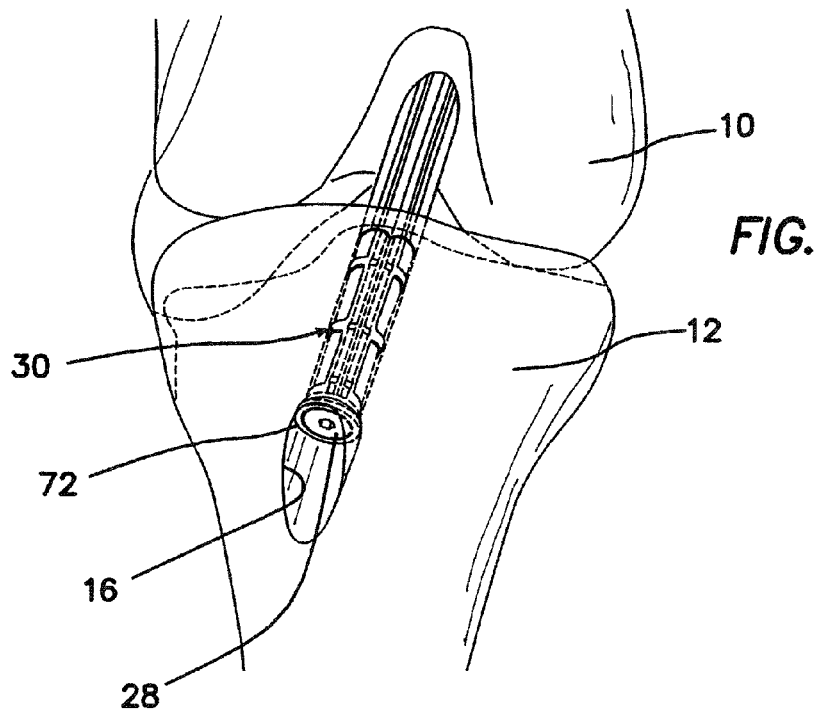
FIG. 39 is a view similar to FIG. 38 wherein the tendon bundles have been trimmed flush with the face of the anchor.
Figure 40:
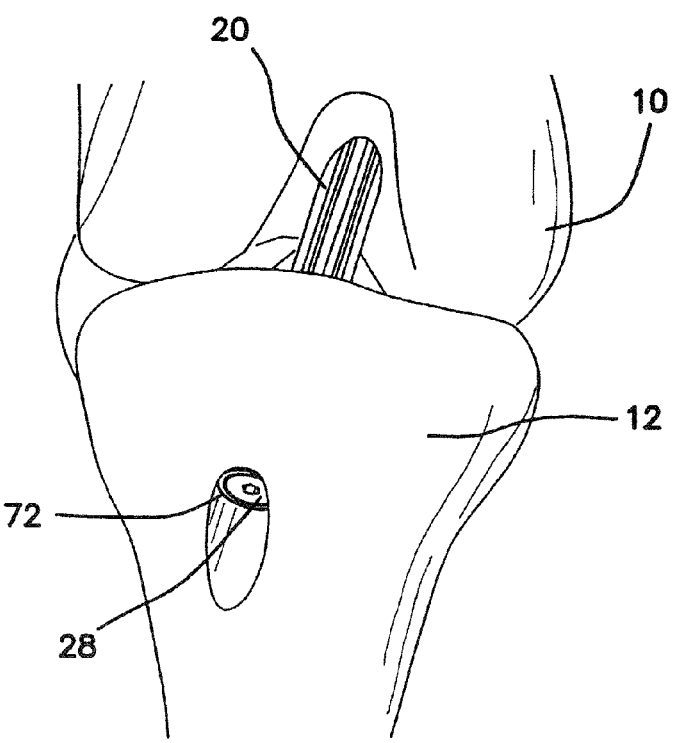
FIG. 40 is a view similar to FIG. 39, except that the removed portions of the bone have been restored in order to shown the patient's knee after the inventive repair procedure has been completed.

FIGS. 39 and 40 illustrate the patient's knee joint once the inventive procedure has been completed. FIG. 39 shows the joint with portions of the bone being removed or transparent so that the entire sheath anchor 30 is visible, while FIG. 40 shows the same joint as it would appear naturally with all bone in place. The final step of the procedure is to trim the protruding ends 88 (FIG. 38) of the tendon bundles 20 so that they are flush with the face of the sheath anchor 30.

Figure 41:
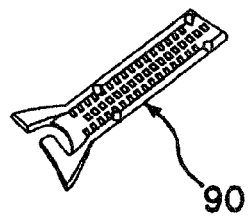
FIG. 41 is a perspective view showing a right anchor portion of another embodiment of a tibial anchor device constructed in accordance with the principles of the present invention.
Figure 42:
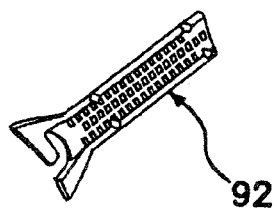
FIG. 42 is a perspective view similar to FIG. 41 showing a left anchor portion of the embodiment of the tibial anchor device of FIG. 41.
Figure 43:
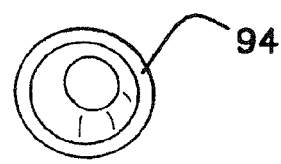
FIG. 43 is a view of a screw retention cup of the tibial anchor device of FIG. 41.
Figure 44:
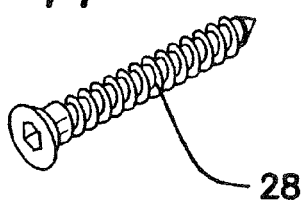
FIG. 44 is a perspective view of a screw for use with the tibial anchor device of FIG. 41.
Figure 45:
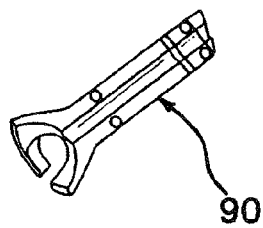
FIG. 45 is a perspective view similar to FIG. 41 of the opposing side of the right anchor portion.
Figure 46:
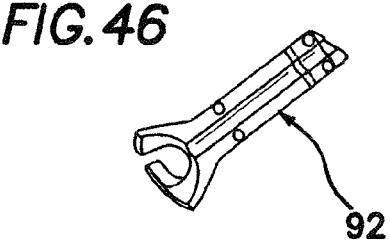
FIG. 46 is a perspective view similar to FIG. 42 of the opposing side of the left anchor portion.
Figure 47:
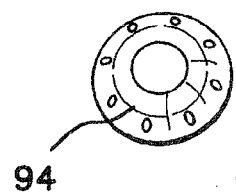
FIG. 47 is a view similar to FIG. 43 of the opposing side of the screw retention cup.

FIGS. 41-47 illustrate components of a second inventive tibial anchor embodiment, which may be identified as a "cone anchor". FIGS. 41 and 45 illustrate opposing sides of a right anchor portion 90 and FIGS. 42 and 46 illustrate opposing sides of a left anchor portion 92. Opposing sides of a generally conical screw retention cup 94 are shown in FIGS. 43 and 47. A screw 28 is shown in FIG. 44. It is noted that, in this embodiment, all like elements to those shown in previous embodiments will bear identical reference numerals.

The procedure for utilizing a cone anchor 96 of FIGS. 41-47 (FIG. 48) to repair a patient's joint 82 is initiated in the same manner as for the sheath anchor 30. Thus, as shown in FIGS. 1-4, a femur hole 18 and tibial tunnel 16 are drilled, and a femoral anchor is inserted and deployed to anchor tendon bundles 20 in place within the femoral hole 18, so that the tendon bundles 20 extend downwardly through the tibial tunnel 16, as shown in FIG. 4. The reader is referred to the description above for further detail regarding this part of the procedure.

Figure 48:
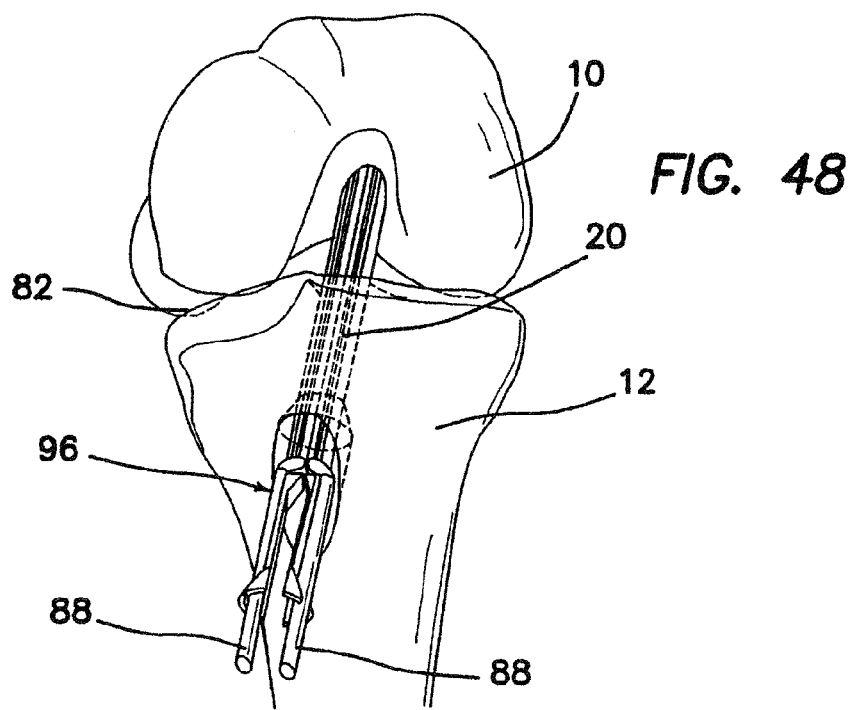
FIG. 48 is a view of a patient's femur and tibia, with portions of the bone removed for ready visualization, showing the tibial anchor of FIGS. 41-47 being installed, by pulling tendon bundles through the left and right anchors.
Figure 49:
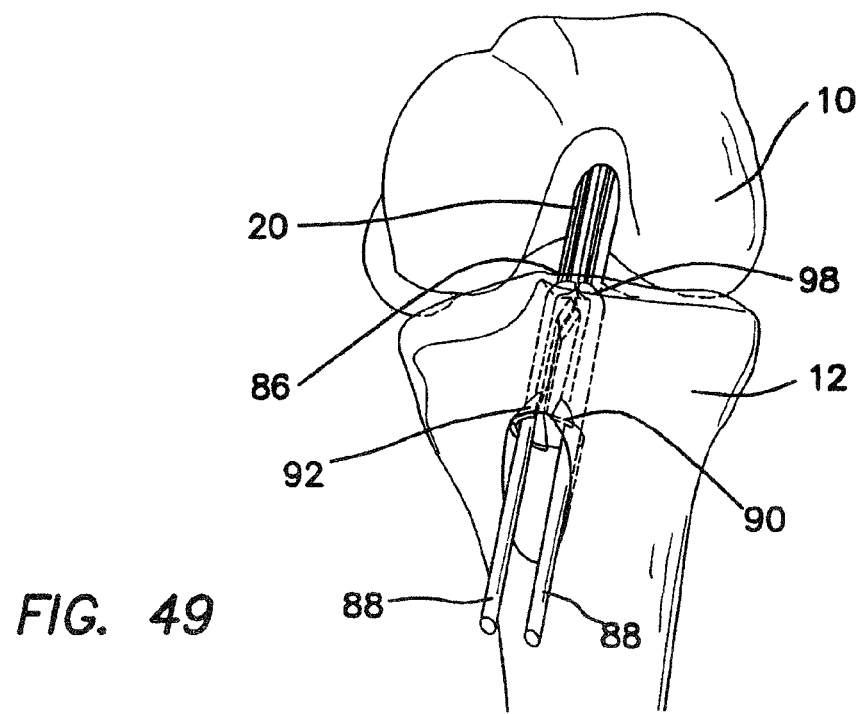
FIG. 49 is a view similar to FIG. 48, wherein the anchor portions are slid up the tendons into the bone hole until the anchor bottoms out against an angular surface in the hole.
Figure 50:
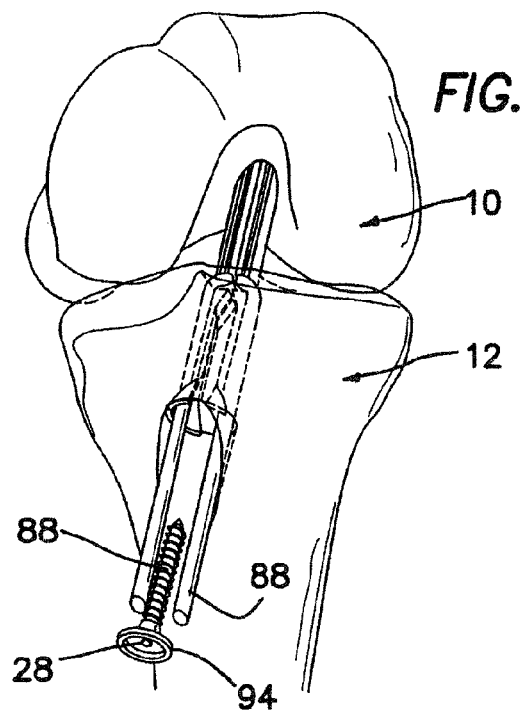
FIG. 50 is a view similar to FIG. 49, wherein the tendons have been tensioned, and the screw and retainer cup tightened.
Figure 51:
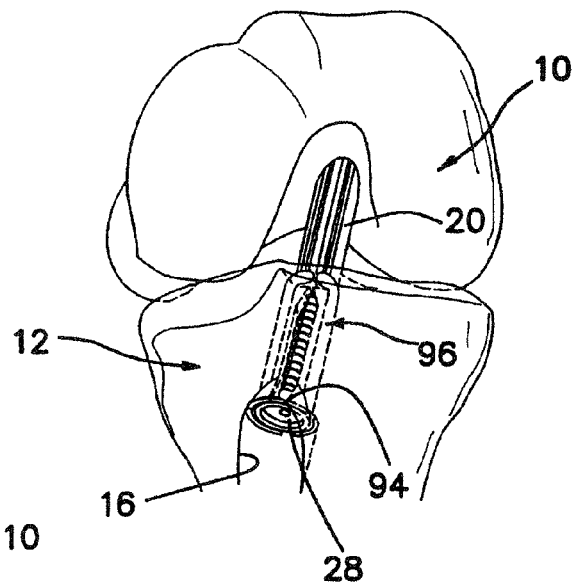
FIG. 51 is a view similar to FIG. 50, wherein the tendon bundles have been trimmed flush with the face of the anchor.
Figure 52:
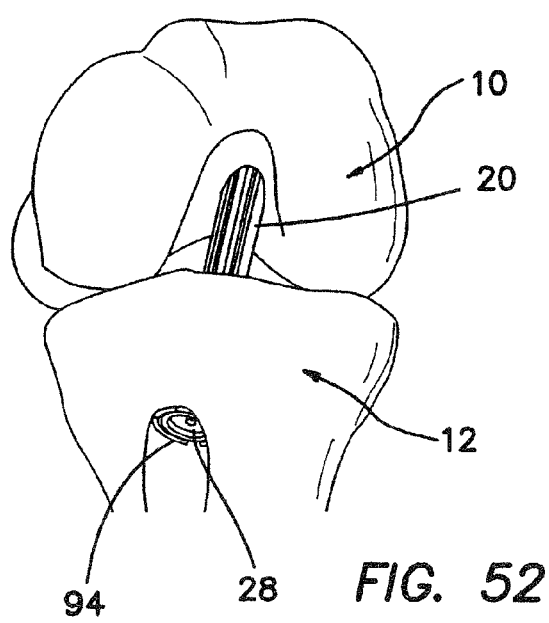
FIG. 52 is a view similar to FIG. 51, except that the removed portions of the bone have been restored in order to shown the patient's knee after the inventive repair procedure has been completed.
Figure 53:
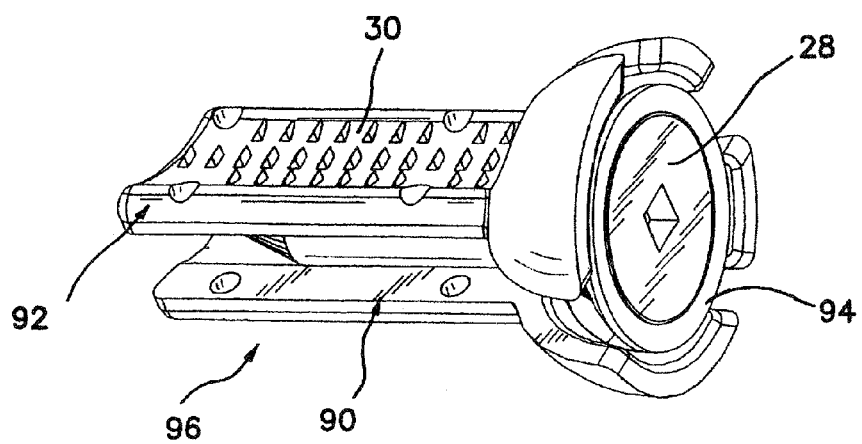
FIG. 53 is a perspective view of a tibial anchor device similar to that shown in FIGS. 41-47, in an assembled configuration.
Figure 54:
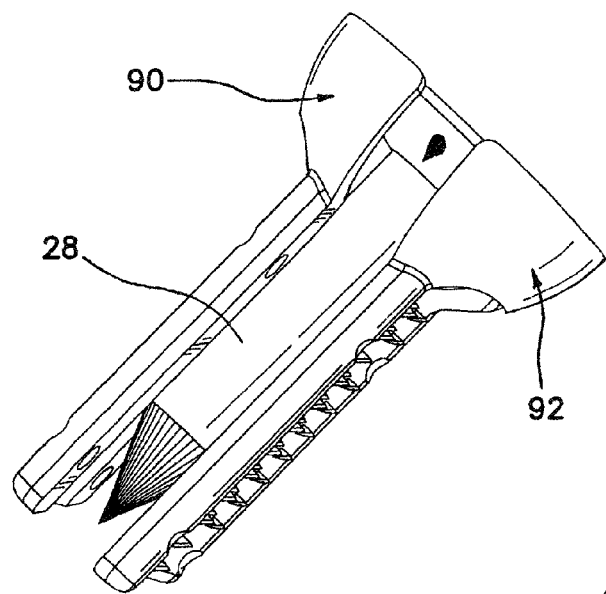
FIG. 54 is another view of the anchor device of FIG. 53.
Figure 55:
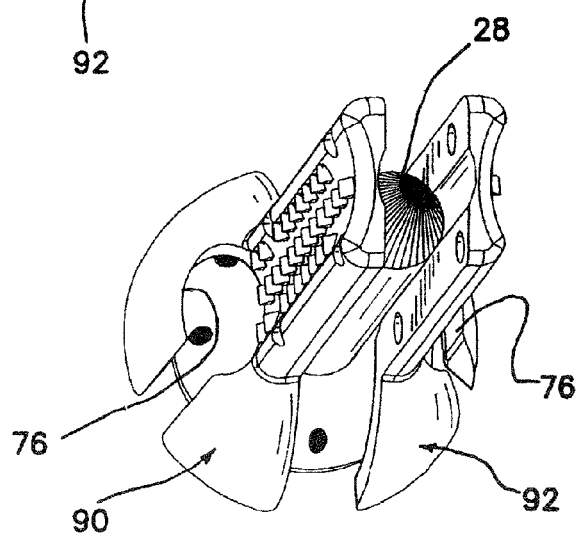
FIG. 55 is still another view of the anchor device of FIGS. 53 and 54.
Figure 56:
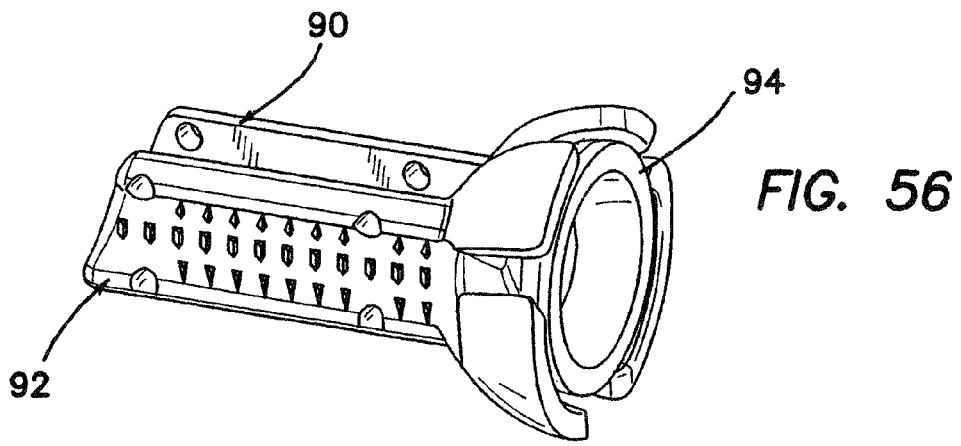
FIG. 56 is yet another view of the anchor device of FIGS. 53-55.
Figure 57:
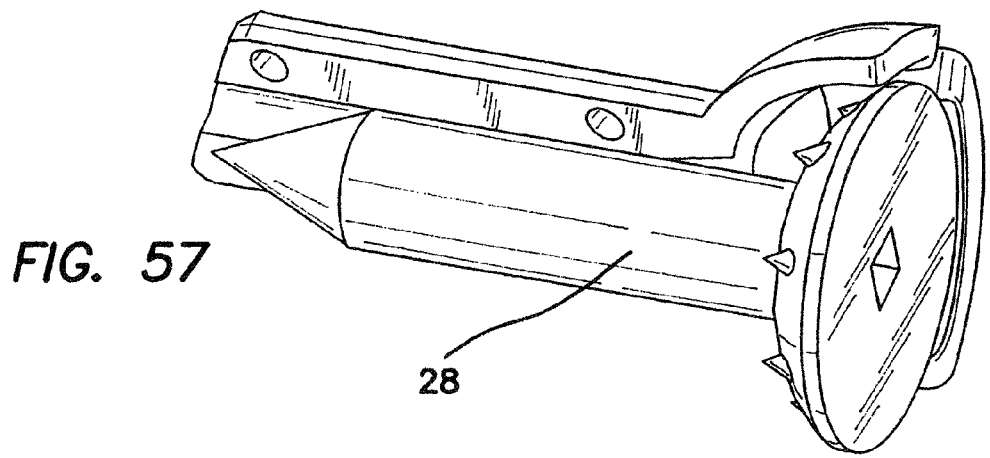
FIG. 57 is a view of the anchor device of FIG. 54-56, wherein some of the anchor portions have been removed for visibility.

Now, as shown in FIG. 48, the tendon bundles 20 are pulled through the cone anchor 96 in order to insert the tibial anchor into the tibial tunnel 16. In this embodiment, the tendon bundles are secured against the anchor portions 90 or 92 because they are pulled through tendon loops 76, which are formed in the proximal end of each anchor half 90, 92, respectively. Then, as shown in FIG. 49, the anchor 96 is slid upwardly along the tendon bundles 20 until the anchor 96 bottoms out against the angular surface in the tibial hole 16, as with the first embodiment. Again, as in the first embodiment, this positioning will cause the distal end 98 of the anchor 96 to be located in close proximity to the distal end 86 of the tibial tunnel 16 so that good aperture fixation will result. Then, as illustrated in FIG. 50, the tendons are appropriately tensioned and the screw 28 is inserted and tightened, together with the retainer cup 94, until seated. This action of inserting and tightening the screw 28 and screw retainer cup 94 will cause the anchor portions 90, 92 to move laterally outwardly in order to engage the tendon bundles 20 between the anchor portions 90, 92 and adjacent tibial bone, as in the sheath anchor embodiment. FIGS. 51 and 52 illustrate the anchor 96 in its fully installed condition, after the tendon ends 88 are trimmed flush and the procedure is otherwise completed.

FIGS. 53-57 illustrate, in somewhat greater detail and in an assembled configuration, a cone anchor 96 of a type very similar to that illustrated in the embodiment of FIGS. 41-52. Like elements are denoted by like reference numbers.

Figure 58:
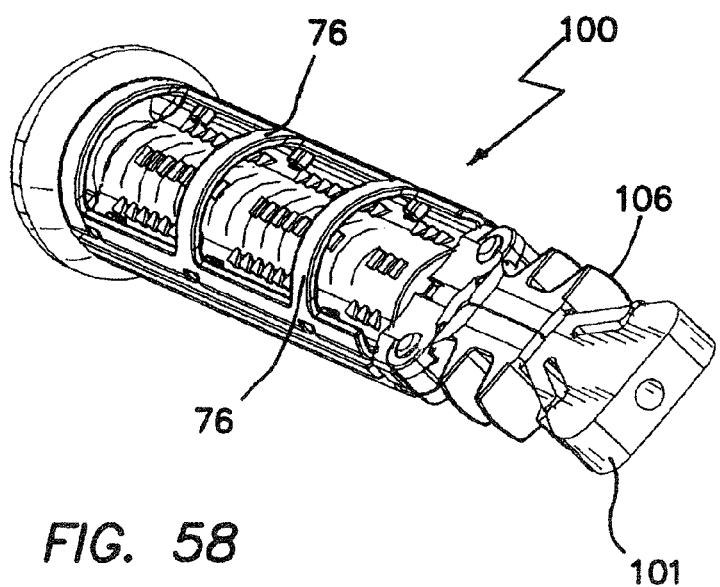
FIG. 58 is a perspective view of yet another tibial anchor embodiment in accordance with the principles of the present invention.

A modified tibial anchor embodiment 100 is illustrated in FIGS. 58-60. This embodiment is similar to prior disclosed embodiments to the extent that there are provided two opposing sheaths having tendon loops 76 disposed thereon. A screw 28 and associated screw retention disk or cup 94 are also provided. Thus, the basic procedural steps for utilizing this anchor 100 are similar to those already described in connection with the previous disclosed embodiments. What is different about this embodiment, in particular, is the provision of a distal wedge 101 which functions to provide positive aperture fixation by ensuring that the anchor will be stopped within the tibial tunnel at an appropriate point during the insertion step. Pivotable arms 102 connect the anchor body to the wedge 101, wherein the arms 102 are pivotable outwardly about hinges 104. Thus, when it is desired to lock the tibial anchor 100 in place within the tibial tunnel, insertion and tightening of the screw 28 within the anchor body actuates the arms 102 to pivot outwardly laterally about the hinges 104, thereby functioning to expand the wedge and cause positive engagement of the wedge and arms 102 with the tendon bundles and adjacent tibial bone. As in prior embodiments, positive fixation is enhanced by the provision of spikes 106 or other suitable means for penetrating the tendon bundles and the bone to lock the tendon bundles and anchor in place.

Accordingly, although an exemplary embodiment of the invention has been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A material fixation system, comprising:
    a first sheath portion and a second sheath portion defining a space therebetween, said first sheath portion and said second sheath portion defining a proximal end, a distal end, a first side, and a second side; wherein said first side and said second side extend between said proximal end and said distal end;
    a hinge for attaching said sheath portions together along one side thereof;
    wherein said hinge is on said first side and said hinge comprises a hinge protrusion placed in a hinge slot; a snap fitting on said second side, said snap fitting comprising a snap post received in a snap hole to keep said first sheath portion and said second sheath portion from opening prematurely;
    a cortical hook on one of said sheath portions for engaging hard cortical bone at the procedural site; and
    an insertion member insertable into said space from said proximal end to said distal end for expanding said first sheath portion and said second sheath portion laterally outwardly in order to urge a soft tissue graft against an adjacent bone surface.

2. The material fixation system as recited in claim 1, wherein said insertion member comprises a tapered screw.

3. The material fixation system as recited in claim 1, wherein said hinge comprises a hinge protrusion disposed on a first of said sheath portions and a hinge slot disposed on a second of said sheath portions, wherein said hinge protrusion and said hinge slot engage one another.

4. The material fixation system as recited in claim 3, and further comprising a second hinge protrusion disposed on said second sheath portion and a second hinge slot disposed on said first sheath portion, wherein said second hinge protrusion and said second hinge slot engage one another.

5. The material fixation system as recited in claim 1, and further comprising a driver for engaging and moving said insertion member.

6. The material fixation system as recited in claim 2, wherein said screw has a bullnose screw head.

7. The material fixation system as recited in claim 1, wherein said two sheath portions are mirror images of one another.

8. The material fixation system as recited in claim 1, wherein said soft tissue graft comprises an autograft.

9. The material fixation system as recited in claim 1, wherein said soft tissue graft comprises an allograft.

10. The material fixation system as recited in claim 2, wherein a distal end of said screw comprises a cut-out portion which permits the distal end of the screw to easily fit between said two sheath portions, thus permitting an operator to easily start rotation of the screw.

11. The material fixation system as recited in claim 2, wherein said screw comprises external threads and said sheath portions comprise complementary internal threads, said screw further comprising a thread start to enable easier engagement of the screw threads and the sheath threads.

12. The material fixation system as recited in claim 1, and further comprising at least one retaining rib on at least one sheath portion for providing small areas of higher force between the sheath portion and the soft tissue graft.

13. The material fixation system as recited in claim 1, wherein said sheath portions and said insertion member are adapted for insertion into a bone tunnel in a patient's tibia, and said soft tissue graft comprises a tendon graft for making an ACL repair.

14. The material fixation system as recited in claim 1, wherein one of said sheath halves comprises a snap post and the other one of said sheath halves comprises a complementary snap hole, said snap post and said snap hole being engageable with one another to keep the two sheath halves from opening prematurely.

15. The material fixation system as recited in claim 1, and further comprising a ramp formed on one of said sheath portions for allowing a tip of the sheath portion to provide compression between the soft tissue graft and the bone at the aperture of bone tunnel in which said system is disposed.

16. The material fixation system as recited in claim 1, and further comprising flex grooves disposed on one of said sheath portions, for permitting the sheath portion to flex and form around a tip of the insertion member.

17. The material fixation system as recited in claim 1, and further comprising a bullnose sheath tip on one of said sheath portions.

18. An implant system for promoting soft tissue to bone contact in order to promote good fixation of soft tissue to bone when making an orthopedic repair of a joint, said implant system comprising:
a first implant adapted for receiving a tissue graft thereon and then being disposed in a first bone tunnel location, wherein ends of the tissue graft extend through a bone tunnel and out of a proximal end of the tunnel;
a second implant adapted for disposition in a second bone tunnel location, proximal to said first bone tunnel location, said second implant having a length, and comprising a plurality of sheath members having laterally outer surfaces and being adapted for advancing to the first bone tunnel location by sliding over the ends of the tissue graft, so that when the second implant is in said second bone tunnel location, the tissue grafts are disposed between the laterally outer surfaces of said plurality of sheath members and the bone defining said bone tunnel;
wherein said plurality of sheath members comprises a first sheath member and a second sheath member defining a space therebetween, said first sheath member and said second sheath member defining a proximal end, a distal end, a first opposed side, and a second opposed side; wherein said first opposed side and said second opposed side extend between said proximal end and said distal end;
a plurality of hinges spaced along the first side of said second implant;
wherein said plurality of hinges is on said first opposed side and each of said plurality of hinges comprises a hinge protrusion placed in a hinge slot;
a plurality of snap fittings spaced along the second opposed side of said second implant; wherein each of said plurality of snap fittings comprises a snap post received in a snap hole to keep said first sheath member and said second sheath member from opening prematurely; and
an insertion member insertable into said space from said proximal end to said distal end for expanding said first sheath member and said second sheath member laterally outwardly toward said soft tissue graft, thereby urging said soft tissue graft into contact with the bone defining said bone tunnel.

19. The implant system as recited in claim 18, wherein said insertion member comprises a tapered screw.

20. The implant system as recited in claim 18, wherein each of said plurality of hinges comprises a hinge protrusion disposed on a first of said sheath portions and a hinge slot disposed on a second of said sheath portions, wherein said hinge protrusion and said hinge slot engage one another.

21. The implant system as recited in claim 18, wherein said plurality of sheath portions are mirror images of one another.

22. The implant system as recited in claim 18, wherein said soft tissue graft comprises an autograft.

23. The implant system as recited in claim 18, wherein said soft tissue graft comprises an allograft.

24. The implant system as recited in claim 19, wherein a distal end of said screw comprises a cut-out portion which permits the distal end of the screw to easily fit between said two sheath portions, thus permitting an operator to easily start rotation of the screw.

25. The implant system as recited in claim 19, wherein said screw comprises external threads and said sheath portions comprise complementary internal threads, said screw further comprising a thread start to enable easier engagement of the screw threads and the sheath threads.

26. The implant system as recited in claim 18, and further comprising at least one retaining rib on at least one sheath portion for providing small areas of higher force between the sheath portion and the soft tissue graft.

27. The implant system as recited in claim 18, and further comprising a cortical hook on one of said sheath portions for engaging hard cortical bone at the procedural site.

28. The implant system as recited in claim 18, each of said snap fittings comprising a snap post on one of said sheath halves and a complementary snap hole on the other one of said sheath halves, said snap post and said snap hole being engageable with one another to keep the two sheath halves from opening prematurely.

29. The implant system as recited in claim 18, and further comprising a ramp formed on one of said sheath portions for allowing a tip of the sheath portion to provide compression between the soft tissue graft and the bone at the aperture of bone tunnel in which said system is disposed.

30. The implant system as recited in claim 18, and further comprising flex grooves disposed on one of said sheath portions, for permitting the sheath portion to flex and form around a tip of the insertion member.

31. A material fixation system, comprising:
a first sheath portion and a second sheath portion defining a space therebetween, said first sheath portion and said second sheath portion defining a proximal end, a distal end, a first side, and a second side; wherein said first side and said second side extend between said proximal end and said distal end, said first sheath portion and said second sheath portion being initially engaged with one another in an undeployed orientation;
a hinge on said first side for initially engaging said first sheath portion and said second sheath portion, said hinge comprising a hinge protrusion placed in a hinge slot;
a second hinge protrusion disposed on said second sheath portion and a second hinge slot disposed on said first sheath portion, wherein said second hinge protrusion and said second hinge slot engage one another;
a cortical hook on one of said sheath portions for engaging hard cortical bone at the procedural site;

a snap fitting on said second side, said snap fitting comprising a snap post received in a snap hole to keep said first sheath portion and said second sheath portion from opening prematurely; and an insertion member insertable into said space from said proximal end to said distal end for expanding said first sheath portion and said second sheath portion laterally outwardly in order to urge a soft tissue graft against an adjacent bone surface;

wherein as said sheath portions expand outwardly to said fully deployed orientation, they become detached from one another.

32. The material fixation system as recited in claim 31, wherein said insertion member comprises a tapered screw.

33. The material fixation system as recited in claim 31, and further comprising a driver for engaging and moving said insertion member.

34. The material fixation system as recited in claim 31, wherein said screw has a bullnose screw head.

35. The material fixation system as recited in claim 31, wherein said two sheath portions are mirror images of one another.

36. The material fixation system as recited in claim 31, wherein said soft tissue graft comprises an autograft.

37. The material fixation system as recited in claim 31, wherein said soft tissue graft comprises an allograft.

38. The material fixation system as recited in claim 31, wherein a distal end of said screw comprises a cut-out portion which permits the distal end of the screw to easily fit between said two sheath portions, thus permitting an operator to easily start rotation of the screw.

39. The material fixation system as recited in claim 31, wherein said screw comprises external threads and said sheath portions comprise complementary internal threads, said screw further comprising a thread start to enable easier engagement of the screw threads and the sheath threads.

40. The material fixation system as recited in claim 31, and further comprising at least one retaining rib on at least one sheath portion for providing small areas of higher force between the sheath portion and the soft tissue graft.

41. The material fixation system as recited in claim 31, wherein said sheath portions and said insertion member are adapted for insertion into a bone tunnel in a patient's tibia, and said soft tissue graft comprises a tendon graft for making an ACL repair.

42. The material fixation system as recited in claim 31, and further comprising a ramp formed on one of said sheath portions for allowing a tip of the sheath portion to provide compression between the soft tissue graft and the bone at the aperture of bone tunnel in which said system is disposed.

43. The material fixation system as recited in claim 31, and further comprising flex grooves disposed on one of said sheath portions, for permitting the sheath portion to flex and form around a tip of the insertion member.

44. The material fixation system as recited in claim 31, and further comprising a bullnose sheath tip on one of said sheath portions.

* * * * *